(12) United States Patent
Kinsho et al.

(10) Patent No.: US 7,192,684 B2
(45) Date of Patent: Mar. 20, 2007

(54) POLYMERIZABLE SILICON-CONTAINING COMPOUND, MANUFACTURING METHOD, POLYMER, RESIST COMPOSITION AND PATTERNING PROCESS

(75) Inventors: Takeshi Kinsho, Niigata-ken (JP); Takeru Watanabe, Niigata-ken (JP); Koji Hasegawa, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 26 days.

(21) Appl. No.: 10/671,732

(22) Filed: Sep. 29, 2003

(65) Prior Publication Data

US 2004/0067436 A1 Apr. 8, 2004

(30) Foreign Application Priority Data

Sep. 30, 2002 (JP) .............................. 2002-285171

(51) Int. Cl.
*G03C 1/73* (2006.01)
*G03F 7/039* (2006.01)
*G03F 7/36* (2006.01)
*C08F 30/08* (2006.01)
*C07F 7/08* (2006.01)

(52) U.S. Cl. .................. 430/270.1; 430/326; 430/905; 430/907; 430/910; 430/311; 430/327; 430/330; 430/331; 526/279; 556/438; 556/439; 556/440; 556/442; 556/443; 556/449; 556/450; 556/453; 556/455; 556/456; 556/457; 556/464; 556/465; 556/482; 556/486; 556/489

(58) Field of Classification Search ............. 430/270.1, 430/326, 905, 907, 910, 311, 313, 327, 330, 430/331; 526/279

See application file for complete search history.

(56) References Cited

U.S. PATENT DOCUMENTS 5,874,511 A * 2/1999 Rizzardo et al. ............ 526/286

FOREIGN PATENT DOCUMENTS

| JP | 56-110693 | * | 9/1981 |
| JP | 62-104823 | * | 5/1987 |
| JP | 5-158239 | A | 6/1993 |
| JP | 5-232706 | A | 9/1993 |
| JP | 5-249662 | A | 9/1993 |
| JP | 5-249683 | A | 9/1993 |
| JP | 5-257282 | A | 10/1993 |
| JP | 5-289322 | A | 11/1993 |
| JP | 5-289340 | A | 11/1993 |
| JP | 6-118651 | A | 4/1994 |
| JP | 9-110938 | A | 4/1997 |

OTHER PUBLICATIONS

JPO English abstract for JP 56-110693.*
Full, formal English translation of JP 56-110693 (Sakurai et al), provided by PTO.*
Haider "A Simple Synthesis of (2-Ethoxycarbonylallyl)trimethylsilane, A Potential Synthon for the Synthesis of 2-Methylene-4-alkanolides", Synthesis (1985) (3), p. 271-2.*
Fleming et al (Chemical Abstract 1982:562257—abstract for "Cycloelimination of beta-silylethyl sulfoxides: alkene, alkyne, and vinylsilane-forming reactions", Journal of the chemical Society, Perkin Transactions 1: Organic and Bio-Organic Chemistry (1972-1999) (7), p. 1563-9).*
JPO English abstract for JP 62-104823 (Eriyama et al).*
SPIE vol. 1925, (1993), p. 377 W. Brunsvold et al.
SPIE vol. 3678, (1999), p. 214 Carl R. Kessel et al.
SPIE vol. 3678, (1999), p. 241 Qinghuang Lin et al.
SPIE vol. 3678, (1999), p. 562 Larry D. Boardman et al.
SPIE vol. 3678, (1999), p. 420 Jin-Break Kim et al.

* cited by examiner

*Primary Examiner*—Sin Lee
(74) *Attorney, Agent, or Firm*—Birch, Stewart, Kolasch and Birch, LLP

(57) ABSTRACT

Polymerizable silicon-containing compounds of formula (1) wherein $R^1$ is hydrogen, halogen or monovalent organic group are polymerized into polymers. A resist composition comprising the polymer as a base resin is sensitive to high-energy radiation, has excellent sensitivity and resolution at a wavelength of less than 300 nm, and high resistance to oxygen plasma etching, and thus lends itself to micro-patterning for the fabrication of VLSIs

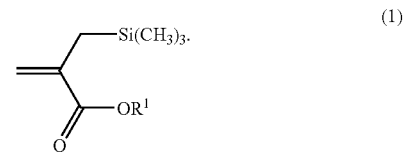

(1)

16 Claims, No Drawings

US 7,192,684 B2

POLYMERIZABLE SILICON-CONTAINING COMPOUND, MANUFACTURING METHOD, POLYMER, RESIST COMPOSITION AND PATTERNING PROCESS

This invention relates to polymers suitable as the base resin in chemically amplified positive resist compositions used for micropatterning in a process for the fabrication of semiconductor devices. It also relates to polymerizable silicon-containing compounds for the polymers and a method of preparing the compounds. It further relates to resist compositions, especially chemically amplified positive resist compositions adapted for exposure to high-energy radiation such as deep-UV, KrF excimer laser light (248 nm), ArF excimer laser light (193 nm), electron beams or x-rays, and a process for forming a pattern.

BACKGROUND OF THE INVENTION

While a number of recent efforts are being made to achieve a finer pattern rule in the drive for higher integration and operating speeds in LSI devices, the commonly used light exposure technology is approaching the essential limit of resolution determined by the light source wavelength. For the light exposure using g-line (436 nm) or i-line (365 nm), a pattern rule of about 0.5 μm is thought to be the limit. The LSI fabricated using such light exposure has a maximum degree of integration corresponding to 16 M-bit dynamic random access memory (DRAM). However, the laboratory fabrication of LSI already reached this stage, and the development of a further micropatterning technology is in urgent demand.

One means for reducing the pattern size is to reduce the wavelength of exposure light used in forming a resist pattern. For the mass production process of 256 M-bit DRAM (processing size up to 0.25 μm), it is now under intensive consideration to replace i-line (365 nm) as the exposure light source by KrF excimer laser light of a shorter wavelength of 248 nm. However, for the fabrication of DRAM with a degree of integration of 1 G or more requiring a finer patterning technology (processing size up to 0.2 μm), a shorter wavelength light source is required, and in particular, photolithography using ArF excimer laser light (193 nm) is now under investigation.

Since H. Ito, G. C. Willson et al of IBM proposed a chemically amplified positive resist composition comprising a resin in the form of polyhydroxystyrene having hydroxyl groups blocked with tert-butoxycarbonyloxy (t-BOC) groups, that is, poly(4-t-butoxycarbonyloxystyrene) (PB-OCST) and a photoacid generator in the form of an onium salt, a number of resist compositions having a high sensitivity and resolution have been developed. These chemically amplified positive resist compositions all have a high sensitivity and resolution, but are difficult to form fine patterns with a high aspect ratio because of the low mechanical strength of the patterns.

A number of chemically amplified positive resist compositions using the above-mentioned polyhydroxystyrene as the base resin and having sensitivity to deep-UV, electron beams and x-rays are known in the art. These resist compositions, however, rely on the single-layer resist method although the bi-layer resist method is advantageous in forming a pattern with a high aspect ratio on a uneven substrate. These resist compositions are not yet practically acceptable because of the outstanding problems of substrate topography, light reflection from substrates, and difficulty of forming high-aspect ratio patterns.

As is known in the art, the bi-layer resist method is advantageous in forming a high-aspect ratio pattern on a uneven substrate. It is also known that in order to develop a bi-layer resist film with a common alkaline developer, hydrophilic groups such as hydroxyl and carboxyl groups must be attached to silicone polymers.

Among silicone based chemically amplified positive resist compositions, recently proposed were those compositions comprising a base resin in the form of polyhydroxybenzylsilsesquioxane, which is a stable and alkali-soluble silicone polymer, in which the part of phenolic hydroxyl group is protected with t-BOC group, in combination with a photoacid generator (see JP-A 6-118651 and SPIE vol. 1925 (1993), 377). Also JP-A 9-110938 discloses a silicone-containing polymer using a silicon-containing acrylic monomer. The silicon-containing polymer of the acrylic pendant type has the drawback that its resistance to dry etching with oxygen plasma is weak as compared with the silsesquioxane polymer. A low silicon content accounts for this weak dry etching resistance. The silicon-containing polymer of the pendant type has drawbacks including developer repellency, poor wetting with developer, weak adhesion to organic film and ease of peeling. To overcome these drawbacks, copolymerization with a (meth)acrylate monomer having an oxygen functional group such as lactone is proposed, but entails the problem that the silicon content is further reduced by introducing the monomer without silicon atom. Then SPIE vol. 3678, pp. 214, 241 and 562 describes a polymer containing a monomer of the trisilane or tetrasilane pendant type having an increased silicon content and a silicon-containing substituent which can be eliminated with acid. However, since compounds having silicon-to-silicon bonds exhibit strong absorption at the wavelength of ArF excimer laser, an increased introduction of such silanes undesirably leads to a lower transmittance. Besides, an attempt of introducing silicon into acid labile groups is reported in SPIE vol. 3678, p. 420. Because of a low acid-catalyzed elimination reactivity, there are drawbacks including low environmental stability and a T-top profile. It is also known that in the case of silicon-containing, acid-eliminatable substituent groups, products (outgases) resulting from elimination have detrimental influence like exposure lens contamination.

SUMMARY OF THE INVENTION

An object of the invention is to provide a novel polymerizable silicon-containing compound which is polymerized into a polymer suited as the resist base resin and a method of preparing the compound.

Another object of the invention is to provide a polymer which is obtained from the compound and useful as the base resin in a chemically amplified positive resist composition for micro-patterning in the semiconductor device fabrication process.

A further object of the invention is to provide a resist composition, especially a chemically amplified positive resist composition, adapted for exposure to high-nergy radiation such as deep-UV, KrF and ArF excimer laser beams (248 and 193 nm), electron beams or x-rays, and a method for forming a pattern using the same.

We have found that compounds having the general formula (1), shown below, are readily prepared by the method to be described below, convertible to various functional derivatives, copolymerizable with other monomers, and polymerizable into polymers having a high transmittance at the relevant wavelength.

In view of the above-discussed problems of the prior art, there exists a need for a polymerizable silicon-ontaining compound (monomer) which possesses silicon substitution at a site to become a polymer backbone after polymerization, is convertible to various functional derivatives, and does not reduce the transmittance at the relevant laser wavelength of a polymer obtained therefrom. The compounds of formula (1) meet these requirements. The compounds make it possible to incorporate silicon into acid labile group-introduced units necessary for resolution and polar group-introduced units necessary for improving developer wetting and substrate adhesion and to increase the silicon content in units having introduced therein silicon-containing groups, without increasing the risk of lens contamination by outgassing. Using the compounds, base polymers having a high silicon content, high sensitivity, high resolution and high aspect ratio for the bi-layer resist technology can be realized. Thus, chemically amplified positive resist compositions capable of forming patterns having heat resistance can be formulated.

In a first aspect, the invention provides a polymerizable silicon-containing compound having the general formula (1):

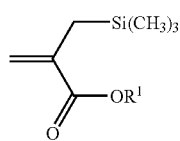
(1)

wherein $R^1$ is a hydrogen atom, halogen atom or monovalent organic group.

One preferred embodiment is a polymerizable silicon-ontaining ester derivative having an acid eliminatable substituent, having the general formula (2):

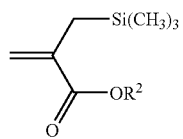
(2)

wherein $R^2$ is an acid labile group.

Another preferred embodiment is a polymerizable silicon-containing ester derivative having a polar group, having the general formula (3):

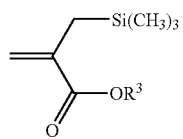
(3)

wherein $R^3$ is a monovalent organic group of 2 to 30 carbon atoms containing an oxygen functional group such as hydroxyl, carbonyl, ether bond or ester bond.

A further preferred embodiment is a polymerizable silicon-containing ester derivative having a silicon-ontaining group, having the general formula (4):

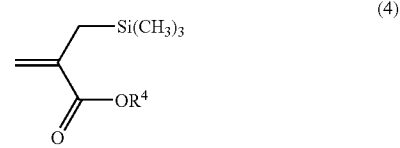
(4)

wherein $R^4$ is a monovalent organic group of 3 to 30 carbon atoms containing at least one silicon atom.

In a second aspect, the invention provides a method for preparing a polymerizable silicon-containing compound having the general formula (B), comprising the steps of reacting an oxalate with a trimethylsilylmethyl-metal compound to form a β-hydroxysilyl compound having the general formula (A) and subjecting the β-hydroxysilyl compound to Peterson elimination reaction.

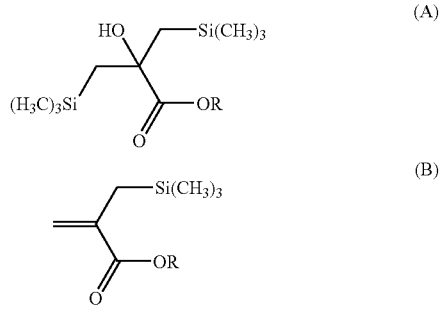

Herein R stands for $R^1$, $R^2$, $R^3$ or $R^4$, $R^1$ is a hydrogen atom, halogen atom or monovalent organic group, $R^2$ is an acid labile group, $R^3$ is a monovalent organic group of 2 to 30 carbon atoms containing an oxygen functional group, and $R^4$ is a monovalent organic group of 3 to 30 carbon atoms containing at least one silicon atom.

In a third aspect, the invention provides a polymer comprising recurring units of the general formula (1a), (2a), (3a) or (4a) and having a weight average molecular weight of 2,000 to 100,000.

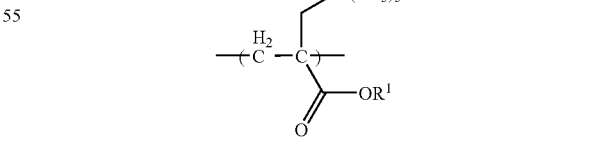
(1a)

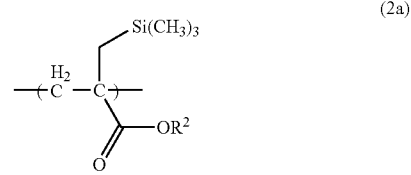
(2a)

-continued

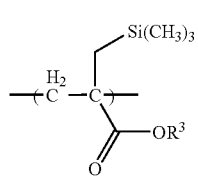
(3a)

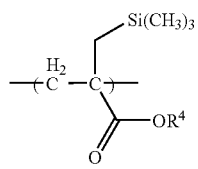
(4a)

Herein R¹, R², R³, and R⁴ are as defined above.

In a preferred embodiment, the polymer further includes recurring units of at least one type having the general formula (5a) or (6a).

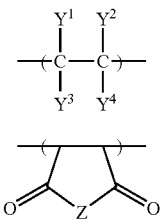
(5a)

(6a)

Herein $Y^1$, $Y^2$, $Y^3$ and $Y^4$ are each independently selected from the group consisting of hydrogen, alkyl groups, aryl groups, halogen atoms, alkoxycarbonyl groups, alkoxycarbonylmethyl groups, cyano groups, fluorinated alkyl groups, and silicon atom-containing monovalent organic groups of 3 to 30 carbon atoms, any two of $Y^1$, $Y^2$, $Y^3$ and $Y^4$ may bond together to form a ring. Z is an oxygen atom or $NR^5$ wherein $R^5$ is hydrogen, hydroxyl or alkyl.

In a fourth aspect, the invention provides a resist composition comprising the polymer defined above, preferably a chemically amplified positive resist composition comprising (A) the polymer defined above, (B) a photoacid generator, and (C) an organic solvent.

In a fifth aspect, the invention provides a method for forming a pattern, comprising the steps of applying the positive resist composition onto an organic film on a substrate to form a coating; prebaking the coating to form a resist film; exposing a circuitry pattern region of the resist film to radiation; post-exposure baking the resist film; developing the resist film with an aqueous alkaline solution to dissolve away the exposed area, thereby forming a resist pattern; and processing the organic film with an oxygen plasma generated by a dry etching apparatus.

DESCRIPTION OF THE PREFERRED EMBODIMENT

Compound

The polymerizable silicon-containing compounds according to the first aspect of the invention have the general formula (1).

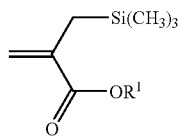
(1)

Herein $R^1$ is a hydrogen atom, a halogen atom or a monovalent organic group. Suitable monovalent organic groups include primary, secondary and tertiary hydrocarbon groups of 1 to 30 carbon atoms, preferably 1 to 15 carbon atoms, cyano, carboxyl and thiol groups. For the hydrocarbon groups, some or all of the hydrogen atoms therein may be substituted with halogen atoms, cyano groups, hydroxyl group, thiol groups or the like; and at least one of a carbonyl group, ether bond, ester bond, sulfide bond, and thiocarbonyl group may intervene between adjacent carbon atoms. Illustrative hydrocarbon groups include straight, branched or cyclic alkyl groups, aryl groups (e.g., phenyl), aralkyl groups (e.g., benzyl), and alkenyl groups (e.g., vinyl, allyl), with the alkyl groups such as methyl and ethyl being most preferred.

The polymerizable silicon-containing compounds of formula (1) include ester derivatives of formula (2) when $R^1$ is $R^2$, ester derivatives of formula (3) when $R^1$ is $R^3$, and ester derivatives of formula (4) when $R^1$ is $R^4$, as will be described below.

One embodiment of the polymerizable silicon-containing compounds is a polymerizable silicon-containing ester derivative of the general formula (2) having an acid eliminatable substituent group which functions as an acid labile unit in a resist polymer.

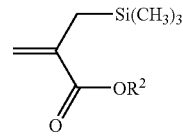
(2)

Herein $R^2$ is an acid labile group.

As used herein, the term "acid labile group" is a group which substitutes for active hydrogen on carboxylic acid and which is cleaved through elimination reaction catalyzed by the acid generated by a photoacid generator at a resist site having undergone light exposure.

Examples of the acid labile group represented by $R^2$ are groups of the following general formulae (L1) to (L3).

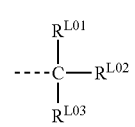
(L1)

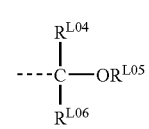
(L2)

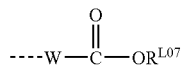

(L3)

In these formulae, the broken line denotes a valence bond. In formula (L1), $R^{L01}$, $R^{L02}$ and $R^{L03}$ are each independently a monovalent hydrocarbon group of chain or alicyclic structure having 1 to 20 carbon atoms, which may contain an ether bond, ester bond or sulfide bond and in which some of the hydrogen atoms may be substituted with halogen atoms, hydroxyl groups, alkoxy groups, carbonyl groups, acyloxy groups, cyano groups or the like. A pair of $R^{L01}$ and $R^{L02}$, $R^{L01}$ and $R^{L03}$, or $R^{L02}$ and $R^{L03}$ may bond together to form a ring. In the ring-forming event, each of $R^{L01}$, $R^{L02}$ and $R^{L03}$ is a divalent hydrocarbon group of chain or alicyclic structure having 1 to 20 carbon atoms, preferably 1 to 15 carbon atoms, which may contain an ether bond, ester bond or sulfide bond and in which some of the hydrogen atoms may be substituted with halogen atoms, hydroxyl groups, alkoxy groups, carbonyl groups, acyloxy groups, cyano groups or the like.

In formula (L2), $R^{L04}$, $R^{L05}$ and $R^{L06}$ are each independently hydrogen or a monovalent hydrocarbon group of chain or alicyclic structure having 1 to 20 carbon atoms, preferably 1 to 15 carbon atoms, which may contain an ether bond, ester bond or sulfide bond and in which some of the hydrogen atoms may be substituted with halogen atoms, hydroxyl groups, alkoxy groups, carbonyl groups, acyloxy groups, cyano groups or the like. A pair of $R^{L04}$ and $R^{L05}$, $R^{L04}$ and $R^{L06}$, or $R^{L05}$ and $R^{L06}$ may bond together to form a ring. In the ring-forming event, each of $R^{L04}$, $R^{L05}$ and $R^{L06}$ is a divalent hydrocarbon group of chain or alicyclic structure having 1 to 20 carbon atoms, preferably 1 to 15 carbon atoms, which may contain an ether bond, ester bond or sulfide bond and in which some of the hydrogen atoms may be substituted with halogen atoms, hydroxyl groups, alkoxy groups, carbonyl groups, acyloxy groups, cyano groups or the like.

$R^{L07}$ is a group of formula (L1) or (L2). W is a divalent hydrocarbon group of chain or alicyclic structure having 1 to 20 carbon atoms, preferably 1 to 15 carbon atoms, which may contain an ether bond, ester bond or sulfide bond and in which some of the hydrogen atoms may be substituted with halogen atoms, hydroxyl groups, alkoxy groups, carbonyl groups, acyloxy groups, cyano groups or the like.

Specific examples of the acid labile group are given below.
t-butyl, t-amyl, 3-methyl-3-pentyl, 3-ethyl-3-pentyl,
2,3-dimethyl-2-butyl, 2-cyclopropyl-2-propyl,
2-cyclopropyl-2-butyl, 3-cyclopropyl-3-pentyl,
2-cyclobutyl-2-propyl, 2-cyclobutyl-2-butyl,
3-cyclobutyl-3-pentyl, 2-cyclopentyl-2-propyl,
2-cyclopentyl-2-butyl, 3-cyclopentyl-3-pentyl,
2-cyclohexyl-2-propyl, 2-cyclohexyl-2-butyl,
3-cyclohexyl-3-pentyl, 2-(1-adamantyl)-2-propyl,
2-(1-adamantyl)-2-butyl, 3-(1-adamantyl)-3-pentyl,
2-(2-adamantyl)-2-propyl, 2-(2-adamantyl)-2-butyl,
3-(2-adamantyl)-3-pentyl,
2-(bicyclo[3.3.1]nonan-9-yl)-2-propyl,
2-(bicyclo[3.3.1]nonan-9-yl)-2-butyl,
3-(bicyclo[3.3.1]nonan-9-yl)-3-pentyl,
2-(2-norbornyl)-2-propyl, 2-(2-norbornyl)-2-butyl,
3-(2-norbornyl)-3-pentyl, 2-(9-oxa-2-norbornyl)-2-propyl,
2-(9-oxa-2-norbornyl)-2-butyl, 3-(9-oxa-2-norbornyl)-3-pentyl,
2-phenyl-2-propyl, 2-phenyl-2-butyl, 3-phenyl-3-pentyl,
1,1-diphenylethyl, 1,1-diphenylpropyl, 1,1-diphenylbutyl,
2-(1-naphthyl)-2-propyl, 2-(1-naphthyl)-2-butyl,
3-(1-naphthyl)-3-pentyl, 2-(2-naphthyl)-2-propyl,
2-(2-naphthyl)-2-butyl, 3-(2-naphthyl)-3-pentyl,
2-(tricyclo[5.2.1.0$^{2,6}$]decan-3-yl)-2-propyl,
2-(tricyclo[5.2.1.0$^{2,6}$]decan-3-yl)-2-butyl,
3-(tricyclo[5.2.1.0$^{2,6}$]decan-3-yl)-3-pentyl,
2-(tricyclo[5.2.1.0$^{2,6}$]decan-4-yl)-2-propyl,
2-(tricyclo[5.2.1.0$^{2,6}$]decan-4-yl)-2-butyl,
3-(tricyclo[5.2.1.0$^{2,6}$]decan-4-yl)-3-pentyl,
2-(tricyclo[5.2.1.0$^{2,6}$]decan-8-yl)-2-propyl,
2-(tricyclo[5.2.1.0$^{2,6}$]decan-8-yl)-2-butyl,
3-(tricyclo[5.2.1.0$^{2,6}$]decan-8-yl)-3-pentyl,
2-(tetracyclo[4.4.0.1$^{2,5}$.1$^{7,10}$]dodecan-3-yl)-2-propyl,
2-(tetracyclo[4.4.0.1$^{2,5}$.1$^{7,10}$]dodecan-3-yl)-2-butyl,
3-(tetracyclo[4.4.0.1$^{2,5}$.1$^{7,10}$]dodecan-3-yl)-3-pentyl,
1-methylcyclopropyl, 1-ethylcyclopropyl, 1-propylcyclopropyl,
1-isopropylcyclopropyl, 1-butylcyclopropyl,
1-(s-butyl)cyclopropyl, 1-(t-butyl)cyclopropyl,
1-pentylcyclopropyl, 1-hexylcyclopropyl,
1-phenylcyclopropyl, 1-benzylcyclopropyl,
1-(1-naphthyl)cyclopropyl, 1-(2-naphthyl)cyclopropyl,
1-methylcyclobutyl, 1-ethylcyclobutyl, 1-propylcyclobutyl,
1-isopropylcyclobutyl, 1-butylcyclobutyl,
1-(s-butyl)cyclobutyl, 1-(t-butyl)cyclobutyl,
1-pentylcyclobutyl, 1-hexylcyclobutyl, 1-phenylcyclobutyl,
1-benzylcyclobutyl, 1-(1-naphthyl)cyclobutyl,
1-(2-naphthyl)cyclobutyl, 1-methylcyclopentyl,
1-ethylcyclopentyl, 1-propylcyclopentyl,
1-isopropylcyclopentyl, 1-butylcyclopentyl,
1-(s-butyl)cyclopentyl, 1-(t-butyl)cyclopentyl,
1-pentylcyclopentyl, 1-hexylcyclopentyl, 1-phenylcyclopentyl,
1-benzylcyclopentyl, 1-(1-naphthyl)cyclopentyl,
1-(2-naphthyl)cyclopentyl, 1-methyl-2-cyclopentenyl,
1-ethyl-2-cyclopentenyl, 1-propyl-2-cyclopentenyl,
1-isopropyl-2-cyclopentenyl, 1-butyl-2-cyclopentenyl,
1-(s-butyl)-2-cyclopentenyl, 1-(t-butyl)-2-cyclopentenyl,
1-pentyl-2-cyclopentenyl, 1-hexyl-2-cyclopentenyl,
1-phenyl-2-cyclopentenyl, 1-benzyl-2-cyclopentenyl,
1-(1-naphthyl)-2-cyclopentenyl,
1-(2-naphthyl)-2-cyclopentenyl, 1-methylcyclohexyl,
1-ethylcyclohexyl, 1-propylcyclohexyl, 1-isopropylcyclohexyl,
1-butylcyclohexyl, 1-(s-butyl)cyclohexyl,
1-(t-butyl)cyclohexyl, 1-pentylcyclohexyl, 1-hexylcyclohexyl,
1-phenylcyclohexyl, 1-benzylcyclohexyl,
1-(1-naphthyl)cyclohexyl, 1-(2-naphthyl)cyclohexyl,
1-methyl-2-cyclohexenyl, 1-ethyl-2-cyclohexenyl,
1-propyl-2-cyclohexenyl, 1-isopropyl-2-cyclohexenyl,
1-butyl-2-cyclohexenyl, 1-(s-butyl)-2-cyclohexenyl,
1-(t-butyl)-2-cyclohexenyl, 1-pentyl-2-cyclohexenyl,
1-hexyl-2-cyclohexenyl, 1-phenyl-2-cyclohexenyl,
1-benzyl-2-cyclohexenyl, 1-(1-naphthyl)-2-cyclohexenyl,
1-(2-naphthyl)-2-cyclohexenyl,
9-methylbicyclo[3.3.1]nonan-9-yl,
9-ethylbicyclo[3.3.1]nonan-9-yl,
2-exo-methyl-2-norbornyl, 2-exo-ethyl-2-norbornyl,
2-exo-propyl-2-norbornyl, 2-exo-isopropyl-2-norbornyl,
2-exo-butyl-2-norbornyl, 2-exo-(s-butyl)-2-norbornyl,
2-exo-(t-butyl)-2-norbornyl, 2-exo-pentyl-2-norbornyl,
2-exo-hexyl-2-norbornyl, 2-exo-phenyl-2-norbornyl, 2-exo-benzyl-2-norbornyl, 2-exo-(1-naphthyl)-2-norbornyl,
2-exo-(2-naphthyl)-2-norbornyl, 2-endo-methyl-2-norbornyl,
2-endo-ethyl-2-norbornyl, 2-endo-propyl-2-norbornyl,
2-endo-isopropyl-2-norbornyl, 2-endo-butyl-2-norbornyl,
2-endo-(s-butyl)-2-norbornyl, 2-endo-(t-butyl)-2-norbornyl,
2-endo-pentyl-2-norbornyl, 2-endo-hexyl-2-norbornyl,
2-endo-phenyl-2-norbornyl, 2-endo-benzyl-2-norbornyl,
2-endo-(1-naphthyl)-2-norbornyl,
2-endo-(2-naphthyl)-2-norbornyl,
8-exo-methyltricyclo[5.2.1.0$^{2,6}$]decan-8-yl,
8-exo-ethyltricyclo[5.2.1.0$^{2,6}$]decan-8-yl,
8-exo-propyltricyclo[5.2.1.0$^{2,6}$]decan-8-yl,
8-exo-isopropyltricyclo[5.2.1.0$^{2,6}$]decan-8-yl,
8-exo-butyltricyclo[5.2.1.0$^{2,6}$]decan-8-yl,
8-exo-(s-butyl)tricyclo[5.2.1.0$^{2,6}$]decan-8-yl,
8-exo-(t-butyl)tricyclo[5.2.1.0$^{2,6}$]decan-8-yl,
8-exo-pentyltricyclo[5.2.1.0$^{2,6}$]decan-8-yl,
8-exo-hexyltricyclo[5.2.1.0$^{2,6}$]decan-8-yl,
8-exo-phenyltricyclo[5.2.1.0$^{2,6}$]decan-8-yl,
8-exo-benzyltricyclo[5.2.1.0$^{2,6}$]decan-8-yl,
8-exo-(1-naphthyl)tricyclo[5.2.1.0$^{2,6}$]decan-8-yl,
8-exo-(2-naphthyl)tricyclo[5.2.1.0$^{2,6}$]decan-8-yl,
8-endo-methyltricyclo[5.2.1.0$^{2,6}$]decan-8-yl,
8-endo-ethyltricyclo[5.2.1.0$^{2,6}$]decan-8-yl,
8-endo-propyltricyclo[5.2.1.0$^{2,6}$]decan-8-yl,
8-endo-isopropyltricyclo[5.2.1.0$^{2,6}$]decan-8-yl,
8-endo-butyltricyclo[5.2.1.0$^{2,6}$]decan-8-yl,
8-endo-(s-butyl)tricyclo[5.2.1.0$^{2,6}$]decan-8-yl,
8-endo-(t-butyl)tricyclo[5.2.1.0$^{2,6}$]decan-8-yl,
8-endo-pentyltricyclo[5.2.1.0$^{2,6}$]decan-8-yl,
8-endo-hexyltricyclo[5.2.1.0$^{2,6}$]decan-8-yl,
8-endo-phenyltricyclo[5.2.1.0$^{2,6}$]decan-8-yl,
8-endo-benzyltricyclo[5.2.1.0$^{2,6}$]decan-8-yl,
8-endo-(1-naphthyl)tricyclo[5.2.1.0$^{2,6}$]decan-8-yl,
8-endo-(2-naphthyl)tricyclo[5.2.1.0$^{2,6}$]decan-8-yl,
3-exo-methyltetracyclo[4.4.0.1$^{2,5}$.1$^{7,10}$]dodecan-3-yl,
3-exo-ethyltetracyclo[4.4.0.1$^{2,5}$.1$^{7,0}$]dodecan-3-yl,
3-exo-propyltetracyclo[4.4.0.1$^{2,5}$.1$^{7,10}$]dodecan-3-yl,
3-exo-isopropyltetracyclo[4.4.0.1$^{2,5}$.1$^{7,10}$]dodecan-3-yl,
3-exo-butyltetracyclo[4.4.0.1$^{2,5}$.1$^{7,10}$]dodecan-3-yl,
3-exo-(s-butyl)tetracyclo[4.4.0.1$^{2,5}$.1$^{7,10}$]dodecan-3-yl,
3-exo-(t-butyl)tetracyclo[4.4.0.1$^{2,5}$.1$^{7,10}$]dodecan-3-yl,
3-exo-pentyltetracyclo[4.4.0.1$^{2,5}$.1$^{7,10}$])dodecan-3-yl,
3-exo-hexyltetracyclo[4.4.0.1$^{2,5}$.1$^{7,10}$]dodecan-3-yl,
3-exo-phenyltetracyclo[4.4.0.1$^{2,5}$.1$^{7,10}$]dodecan-3-yl,
3-exo-benzyltetracyclo[4.4.0.1$^{2,5}$.1$^{7,10}$]dodecan-3-yl,
3-exo-(1-naphthyl)tetracyclo[4.4.0.1$^{2,5}$.1$^{7,10}$]dodecan-3-yl,
3-exo-(2-naphthyl)tetracyclo[4.4.0.1$^{2,5}$.1$^{7,10}$]dodecan-3-yl,
3-endo-methyltetracyclo[4.4.0.1$^{2,5}$.1$^{7,10}$]dodecan-3-yl,
3-endo-ethyltetracyclo[4.4.0.1$^{2,5}$.1$^{7,10}$]dodecan-3-yl,
3-endo-propyltetracyclo[4.4.0.1$^{2,5}$.1$^{7,10}$]dodecan-3-yl,
3-endo-isopropyltetracyclo[4.4.0.1$^{2,5}$.1$^{7,10}$]dodecan-3-yl,
3-endo-butyltetracyclo[4.4.0.1$^{2,5}$.1$^{7,10}$]dodecan-3-yl,
3-endo-(s-butyl)tetracyclo[4.4.0.1$^{2,5}$.1$^{7,10}$]dodecan-3-yl,
3-endo-(t-butyl)tetracyclo[4.4.0.1$^{2,5}$.1$^{7,10}$]dodecan-3-yl,
3-endo-pentyltetracyclo[4.4.0.1$^{2,5}$.1$^{7,10}$]dodecan-3-yl,
3-endo-hexyltetracyclo[4.4.0.1$^{2,5}$.1$^{7,10}$]dodecan-3-yl,
3-endo-phenyltetracyclo[4.4.0.1$^{2,5}$.1$^{7,10}$]dodecan-3-yl,
3-endo-benzyltetracyclo[4.4.0.1$^{2,5}$.1$^{7,10}$]dodecan-3-yl,
3-endo-(1-naphthyl)tetracyclo[4.4.0.1$^{2,5}$.1$^{7,10}$]dodecan-3-yl,
3-endo-(2-naphthyl)tetracyclo[4.4.0.1$^{2,5}$.1$^{7,10}$]dodecan-3-yl,
1-cyclopropylcyclopentyl, 1-cyclobutylcyclopentyl,
1-cyclopentylcyclopentyl, 1-cyclohexylcyclopentyl,
1-(2-norbornyl)cyclopentyl,
1-(2-tetrahydrofuranyl)cyclopentyl,
1-(9-oxa-2-norbornyl)cyclopentyl,
1-(tetracyclo[4.4.0.1$^{2,5}$.1$^{7,10}$]dodecan-3-yl)cyclopentyl,
1-cyclopropylcyclohexyl, 1-cyclobutylcyclohexyl,
1-cyclopentylcyclohexyl, 1-cyclohexylcyclohexyl,
1-(2-norbornyl)cyclohexyl, 1-(2-tetrahydrofuranyl)cyclohexyl,
1-(9-oxa-2-norbornyl)cyclohexyl,
1-(tetracyclo[4.4.0.1$^{2,5}$.1$^{7,10}$]dodecan-3-yl)cyclohexyl,
1-ethoxyethyl, tetrahydrofuranyl, tetrahydropyranyl, etc.

Another embodiment of the polymerizable silicon-containing compounds is a polymerizable silicon-containing ester derivative of the general formula (3) having a polar group (R$^3$) which functions as a unit for imparting such properties as developer affinity, solubility, and substrate adhesion to a resist polymer for tailoring resist properties.

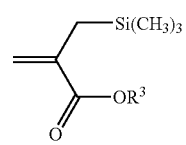

(3)

Herein R$^3$ is a monovalent organic group of 2 to 30 carbon atoms containing an oxygen functional group such as hydroxyl, carbonyl, ether bond or ester bond. Illustrative of the polar group R$^3$ are straight, branched or cyclic hydrocarbon groups of 2 to 30 carbon atoms having a hydroxyl, alkoxy, carboxyl or alkoxycarbonyl group substituted thereon, and monovalent hydrocarbon groups of 3 to 15 carbon atoms having a lactone structure. Specific examples include hydroxyethyl, hydroxypropyl, hydroxybutyl, hydroxypentyl, hydroxyhexyl, hydroxycyclohexyl, hydroxynorbornyl, hydroxytricyclodecanyl, hydroxytetrahydrododecanyl, hydroxyadamantyl, 2,3-dihydroxypropyl, (5-hydroxynorbornan-2-yl)methyl, 3-hydroxy-2,3-dimethyl-2-butyl, methoxymethyl, 2-methoxyethyl, ethoxymethyl, furfuryl, tetrahydrofurfuryl, methoxymethyladamantyl, (1,3-dioxolan-4-yl)methyl, 1,3-dioxan-5-yl, glycidyl, 2-(2-methoxyethoxy)ethyl, (5,6-dihydroxynorbornen-2-yl)methyl, (5-formyloxynorbornan-2-yl)methyl, (6-formyloxynorbornan-2-yl)methyl, (7-oxanorbornan-2-yl)methyl, (2,2-dimethyl-1,3-dioxolan-4-yl)methyl, acetonyl, 3-oxocyclohexyl, 4-oxocyclohexyl, 1-methyl-4-oxocyclohexyl, carboxylmethyl, methoxycarbonylmethyl, 1-carboxyl-2-propyl, 4-carboxylcyclohexyl, 4-carboxy-3-methylcyclohexyl, 4-methoxycarbonylcyclohexyl, 4-ethoxycarbonylcyclohexyl, 4-methoxycarbonyl-3-methylcyclohexyl, (1-ethylcyclopentyl)oxycarbonylmethyl, 5-(1-ethylcyclopentyl)oxycarbonylnorbornan-2-yl, 1-(ethoxycarbonylmethyl)cyclohexyl, 1-(ethoxycarbonyl)ethyl, 5-carboxyl-2-methylbicyclo[2.2.2]octan-2-yl, 5-carboxylbicyclo[2.2.2]octan-2-yl, 5-carboxylnorbornen-2-yl, 2-acetoxyethyl, 2-formyloxyethyl, 2,3-diacetoxypropyl, acetoxyadamantyl, 2,3-formyloxypropyl, (5,6-diformyloxynorbornen-2-yl)methyl, 2-oxooxolan-3-yl, 4,4-dimethyl-2-oxooxolan-3-yl, 5-methyl-2-oxooxolan-5-yl, 2-oxooxolan-4-yl, 4-oxatricyclo[4.2.1.0$^{3,7}$]nonan-5-on-2-yl, 9-methoxycarbonyl-4-oxatricyclo[4.2.1.0$^{3,7}$]nonan-5-on-2-yl, 4,8-dioxatricyclo[4.2.1.0$^{3,7}$]nonan-5-on-2-yl, 9-(2-hydroxy-2-propyl)-4-oxatricyclo[4.2.1.0$^{3,7}$]nonan-5-on-2-yl, spiro[norbornane-2,3'-tetrahydrofuran-2-on]-5-yl, spiro[norbornane-2,3'-tetrahydrofuran-2-on]-6-yl, 5,5-tetramethylene-4-oxatricyclo[5.2.1.0$^{2,6}$]decan-3-on-8-yl, 5,5-tetramethylene- 4-oxatricyclo[5.2.1.0$^{2,6}$]decan-3-on-9-yl, 4-methyloxan-2-on-4-yl, 4-oxatricyclo[5.2.1.0$^{2,6}$]decan-3-on-8-yl, 4-oxatricyclo[5.2.1.0$^{2,6}$]decan-3-on-9-yl, 4-oxatricyclo[5.2.2.0$^{2,6}$]undecan-3-on-8-yl, 4-oxatricyclo[5.2.2.0$^{2,6}$]undecan-3-on-9-yl, 4-oxatricyclo[4.2.1.0$^{3,7}$]nonan-5-on-9-ylmethyl, (2-oxo-1,3-dioxolan-4-yl)methyl, 2-methoxycarbonyloxyethyl, etc.

A further embodiment of the polymerizable silicon-ontaining compounds is a polymerizable silicon-ontaining ester derivative of the general formula (4) having a silicon-containing group ($R^4$) which functions as a unit for increasing a silicon content in a resist polymer.

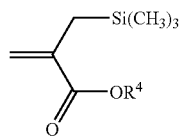

(4)

In formula (4), $R^4$ is a monovalent organic group of 3 to 30 carbon atoms containing at least one silicon atom, preferably 1 to 10 silicon atoms, more preferably 1 to 8 silicon atoms.

Examples of the silicon-containing organic group represented by $R^4$ are given below.

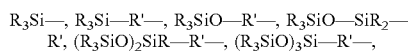

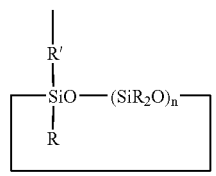

Herein, R is an alkyl group of 1 to 20 carbon atoms or an aryl group of 6 to 20 carbon atoms, with methyl, ethyl and phenyl being preferred. R' is an alkylene group of 1 to 10 carbon atoms, preferably 1 to 5 carbon atoms. The subscript n is at least 2, preferably such a number that the number of silicon atoms falls in the above-specified range.

The silicon-containing organic group represented by $R^4$ may or may not be acid eliminatable. Examples include trimethylsilyl, trimethylsilylmethyl, trimethylsilyloxydimethylsilylmethyl, 1-(trimethylsilyl)ethyl, 1-(trimethylsilyloxydimethylsilyl)ethyl, 2-(trimethylsilyl)ethyl, 2-(trimethylsilyloxydimethylsilyl)ethyl, 2-[bis(trimethylsilyloxy)methylsilyl]ethyl, 2-[tris(trimethylsilyloxy)silyl]ethyl, 2-[tris(trimethylsilyl)silyl]ethyl, 2-(trimethylsilyl)propyl, 2-(trimethylsilyloxydimethylsilyl)propyl, 3-(trimethylsilyl)propyl, 3-(trimethylsilyloxydimethylsilyl)propyl, 3-[bis(trimethylsilyloxy)methylsilyl]propyl, 3-[tris(trimethylsilyloxy)silyl]propyl, 3-[tris(trimethylsilyl)silyl]propyl, 3-[1,1,3,3,5,5,5-heptamethyltrisiloxan-1-yl]propyl, [1,3,3,5,5-pentamethylcyclotrisiloxan-1-yl]propyl, 1-trimethylsilyl-2-propyl, 1-(trimethylsilyldimethylsilyl)-2-propyl, 1-[bis(trimethylsilyloxy)methylsilyl]-2-propyl, 1-[tris(trimethylsilyloxy)silyl]-2-propyl, 1-[tris(trimethylsilyl)silyl]-2-propyl, 1,3-bis(trimethylsilyl)-2-propyl, 2-methyl-1-trimethylsilyl-2-propyl, 1-(trimethylsilylmethyl)cyclopentyl, 1-(trimethylsilylmethyl)cyclohexyl, and the foregoing groups in which the methyl substituent group on a silicon atom in the structure is replaced by another group such as a hydrogen atom, ethyl, n-propyl or isopropyl group.

The silicon-containing compounds of formula (1) (and formulae (2) to (4)), that is, the compounds of formula (B), shown below, can be prepared by reacting an oxalate with a trimethylsilylmethyl-metal compound to form a β-hydroxysilyl compound having the general formula (A) and subjecting the β-hydroxysilyl compound to Peterson elimination reaction. Referring to the method of preparing polymerizable silicon-containing compounds of formula (B), the first step is the reaction of an oxalic diester of formula (C) with 2 equivalents of a trimethylsilylmethyl-metal compound whereby a β-hydroxysilyl compound of formula (A) is formed in high yields.

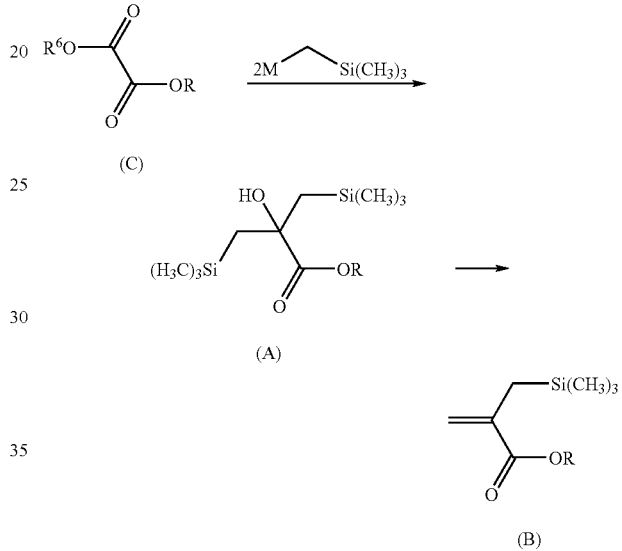

Herein R is as defined for $R^1$, $R^2$, $R^3$ or $R^4$. $R^6$ is an alkyl group which may be the same or different from R. M is Li or MgX wherein X is a halogen atom.

The oxalic diesters as the starting reactant may be either those of formula (C) wherein R and $R^6$ are identical (symmetric esters) or those of formula (C) wherein R and $R^6$ are different (asymmetric esters). Symmetric esters are preferable in that the same product is yielded when reaction takes place at any of the carbonyl groups. Examples of the symmetric esters which are commercially available include dimethyl oxalate, diethyl oxalate, di-n-butyl oxalate, di-t-butyl oxalate, and diphenyl oxalate. If not commercially available, an appropriate symmetric ester may be prepared from oxalyl chloride and an alcohol (ROH). The asymmetric ester wherein R and $R^6$ are different may be prepared, for example, by reacting a chloroglyoxylic ester with an alcohol (ROH) as shown below.

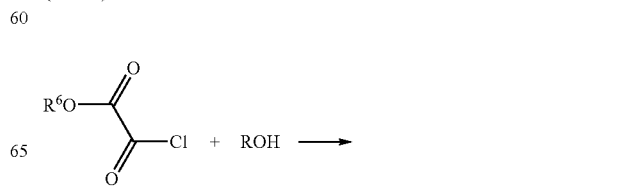

-continued

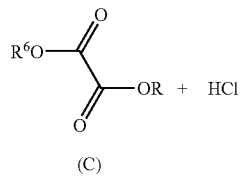

(C)

As the chloroglyoxylic ester used herein, methyl chloroglyoxylate and ethyl chloroglyoxylate are available at low costs. The asymmetric ester is advantageous if the alcohol (ROH) used is expensive and in that where R is a tertiary alkyl group and $R^6$ is methyl or ethyl, a product (A) having undergone reaction on the primary ester side is yielded at a high selectivity (a distinction between two carbonyl groups of oxalic ester (C)).

As the trimethylsilylmethyl-metal compound, trimethylsilylmethyllithium, trimethylsilylmethylmagnesium chloride, and trimethylsilylmethylmagnesium bromide are preferred because they can be prepared from readily available reactants by conventional techniques. There may be co-present metal salts such as cerium (III) chloride.

A solvent is often used in the reaction. For example, an ether solvent such as tetrahydrofuran, diethyl ether or di-n-butyl ether may be used alone or in combination with a hydrocarbon solvent such as hexane, heptane, benzene, toluene, xylene or cumene.

The reaction temperature varies with the structure of reactants. A temperature from −78° C. to the reflux temperature of the solvent, especially from −20° C. to room temperature is preferred for the fast progress of reaction, selectivity of reaction and ease of industrial implementation.

The reaction time is desirably determined by monitoring the reaction until the completion by gas chromatography (GC) or thin-layer chromatography (TLC). The reaction time is usually about 30 minutes to about 18 hours.

Upon reaction of the dialkyl oxalate with the trimethylsilylmethyl-metal compound, the method of mixing them may be by adding dropwise a solution of the dialkyl oxalate to a solution of the trimethylsilylmethyl-metal compound or inversely, by adding dropwise a solution of the trimethylsilylmethyl-metal compound to a solution of the dialkyl oxalate. In either case, the target compound (C) is formed with a high selectivity.

As used herein, the term "selectivity" means that after one molecule of the trimethylsilylmethyl-metal compound reacts with the dialkyl oxalate to presumably form a keto-ester intermediate (D) having two carbonyl groups, nucleophilic addition of a second molecule of the trimethylsilylmethyl-metal compound to the keto-ester intermediate (D) takes place such that the attack to keto-carbonyl group is preferred over the attack to ester carbonyl group.

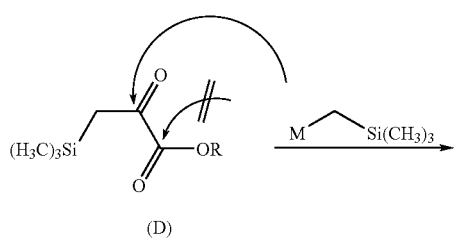

(D)

-continued

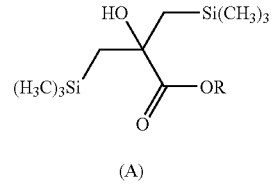

(A)

It is noted that acidic methylene between silyl and carbonyl groups is present in the intermediate (D). If proton is withdrawn from this methylene by the basicity of an organometallic reagent, an enolate is formed, from which the ketone (C) is regenerated after work-up process. Reaction conditions are selected such that the preferable nucleophilic addition reaction to the carbonyl precedes the enolization reaction.

Presumably, due to these two factors, those are, the distinction between two carbonyl groups of intermediate (D) and the progress of nucleophilic addition reaction without enolization, high yields are accomplished.

The second step is to convert the intermediate (A) to the target compound (B). The formation of alkene from β-hydroxysilyl compound through β-elimination is known as Peterson reaction or olefination. Various conditions for Peterson reaction are applicable. The intermediate (A) may be isolated, or direct elimination from the nucleophile adduct of the first step can be employed directly without isolation.

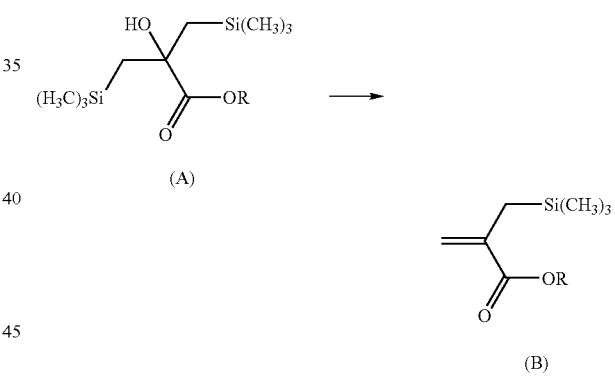

For example, elimination may be promoted by heating the nucleophile adduct of the first step, that is, the lithium or magnesium alkoxide at a temperature in the range from room temperature to the boiling point of the solvent used, or by treating with acetyl chloride or thionyl chloride. Alternatively, the isolated intermediate (A) may be heated or reacted with an acid or base.

Examples of the acid used herein include organic acids such as formic acid, acetic acid, propionic acid, oxalic acid, benzoic acid, benzenesulfonic acid, and p-toluenesulfonic acid; inorganic acids such as hydrochloric acid, hydrobromic acid, sulfuric acid, and nitric acid; and acidic salts such as sodium hydrogen sulfate, potassium hydrogen sulfate and ammonium sulfate.

Examples of the base used herein include organic bases such as triethylamine, diisopropylethylamine, N,N-dimethylaniline, pyridine, 4-dimethylaminopyridine (DMAP), 1,5-diazabicyclo[4.3.0]-5-nonene (DBN), 1,4-diazabicyclo[2.2.2]octane (DABCO), and 1,8-diazabicyclo[5.4.0]-7- undecene (DBU); hydrides such as lithium hydride, sodium hydride, and potassium hydride; hydroxides such as lithium hydroxide, sodium hydroxide, potassium hydroxide, and barium hydroxide; alkoxides such as sodium methoxide, lithium methoxide, potassium methoxide, sodium ethoxide, lithium ethoxide, potassium ethoxide, lithium t-butoxide, and potassium t-butoxide; and basic salts such as sodium acetate, potassium acetate, sodium carbonate, potassium carbonate, and sodium hydrogen carbonate.

Reaction conditions vary with particular reactants and reagents used. For example, where R in the target compound is a tertiary alkyl group, acidic conditions should be avoided so as to prevent elimination of R. Preferred reaction ways for the nucleophile adduct of the first step, that is, alkoxide include treatment with acetyl chloride or thionyl chloride, treatment with potassium t-butoxide in toluene or tetrahydrofuran, treatment with sodium acetate in acetic acid, heating in toluene in the presence of a catalytic amount of p-toluenesulfonic acid, treatment with DBU without solvent, heat treatment in an aqueous acetic acid solution, and two phase reaction of aqueous sodium hydroxide and tetrahydrofuran.

The reaction temperature varies with particular reactants and reagents used. Reaction preferably proceeds at a temperature in the range from room temperature to the boiling point of the solvent.

The reaction time is desirably determined by monitoring the reaction until the completion by gas chromatography (GC) or thin-layer chromatography (TLC). The reaction time is usually about 30 minutes to about 18 hours.

The thus obtained polymerizable silicon-containing ester compound (e.g., R=alkyl) can be converted to a carboxylic acid (R=H) through hydrolysis or elimination reaction. Also, from the ester or carboxylic acid, an ester having a different substituent group R can be synthesized. For the ester synthesis, various well-known conversion reactions including acid-catalyzed esterification reaction between a carboxylic acid and an alcohol, reaction of a corresponding acid chloride with an alcohol under basic conditions, and transesterification reaction from an ester and an alcohol to another ester are applicable, resulting in various ester derivatives.

The polymerizable silicon-containing compound of the invention is copolymerizable with another polymerizable compound or compounds. Typical polymerizable compounds for copolymerization (or comonomers) include those of the formulae (5) and (6).

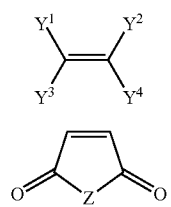

Herein $Y^1$, $Y^2$, $Y^3$ and $Y^4$, which may be the same or different, are independently hydrogen atoms, alkyl groups, aryl groups, halogen atoms, alkoxycarbonyl groups, alkoxycarbonylmethyl groups, cyano groups, fluorinated alkyl groups, or silicon atom-containing monovalent organic groups of 4 to 30 carbon atoms, and any two of $Y^1$, $Y^2$, $Y^3$ and $Y^4$ may bond together to form a ring. Z is an oxygen atom or $NR^5$ wherein $R^5$ is hydrogen, hydroxyl or alkyl.

Of the groups represented by $Y^1$ to $Y^4$, alkyl groups are usually those of 1 to 20 carbon atoms, preferably 1 to 5 carbon atoms. Aryl groups are usually those of 6 to 20 carbon atoms, preferably 6 to 10 carbon atoms, such as phenyl. Preferred halogen atoms are fluorine and chlorine atoms. Alkoxycarbonyl groups are those of 2 to 20 carbon atoms, preferably 2 to 10 carbon atoms. Alkoxycarbonylmethyl groups are those of 3 to 21 carbon atoms, preferably 3 to 11 carbon atoms. Silicon atom-containing organic groups are as exemplified for $R^4$. The alkyl groups represented by $R^5$ are those of 1 to 10 carbon atoms, especially 1 to 5 carbon atoms.

Preferred examples of the comonomer of formula (5) include carboxylic acids such as acrylic acid, methacrylic acid, itaconic acid, crotonic acid, maleic acid, methylenemalonic acid, and α-trifluoromethylacrylic acid, and esters thereof, nitriles such as acrylonitrile and methacrylonitrile, aromatics such as styrene, α-methylstyrene and indene, and silanes having a polymerizable substituent group such as vinylsilane and allylsilane.

Preferred examples of the comonomer of formula (6) include maleic anhydride, maleimide, N-hydroxymaleimide, and N-alkylmaleimides.

Polymers or high molecular weight compounds are generally prepared by furnishing predetermined amounts of a polymerizable silicon-containing compound(s) of formula (1), (2), (3) or (4) and optionally, a comonomer(s) of formulae (5) or (6), mixing the monomers in a solvent, adding a catalyst, and effecting polymerization reaction while heating or cooling if necessary. The polymerization reaction depends on the type of initiator (or catalyst), initiation method (light, heat, radiation or plasma), and polymerization conditions (including temperature, pressure, concentration, solvent and additive). Commonly used for the preparation of the inventive polymer are a radical copolymerization utilizing a radical initiator such as 2,2'-azobisisobutyronitrile (AIBN) etc. and an ionic polymerization (anionic polymerization) using alkyl lithium catalysts. In either mode, polymerization can be done in a conventional manner.

Resist Composition

The polymer of the invention is suitable as a base resin in a resist composition. Thus the invention provides a resist composition comprising the polymer. More specifically, the resist composition is defined herein as comprising (A) the polymer as a base resin, (B) a photoacid generator, (C) an organic solvent, and optionally (D) a dissolution inhibitor, (E) a basic compound and other components.

Organic Solvent (C)

The organic solvent used herein may be any organic solvent in which the base resin (the inventive polymer), photoacid generator, dissolution inhibitor and other components are soluble. Illustrative, non-limiting, examples of the organic solvent include ketones such as cyclohexanone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether, 1-ethoxy-2-propanol and ethyl lactate because the photoacid generator is most soluble therein, propylene glycol monomethyl ether acetate because it is a safe solvent, or a mixture thereof.

Photoacid Generator (B)

Suitable examples of the photoacid generator (B) include onium salts of formula (7) below, diazomethane derivatives of formula (8) below, glyoxime derivatives of formula (9) below, β-ketosulfone derivatives, disulfone derivatives, nitrobenzylsulfonate derivatives, sulfonic acid ester derivatives, and imidoyl sulfonate derivatives.

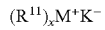  (7)

In the formula, $R^{11}$ is a straight, branched or cyclic alkyl of 1 to 12 carbon atoms, an aryl of 6 to 12 carbon atoms, or an aralkyl of 7 to 12 carbon atoms; $M^+$ is iodonium or sulfonium; $K^-$ is a non-nucleophilic counter-ion; and the letter x is 2 or 3.

Illustrative examples of alkyl groups represented by $R^{11}$ include methyl, ethyl, propyl, butyl, cyclohexyl, 2-oxocyclohexyl, norbornyl, and adamantyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary aralkyl groups include benzyl and phenethyl. Examples of the non-nucleophilic counter-ion represented by $K^-$ include halide ions such as chloride and bromide; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; and alkylsulfonate ions such as mesylate and butanesulfonate.

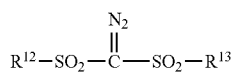  (8)

In the formula, $R^{12}$ and $R^{13}$ are straight, branched or cyclic alkyl or halogenated alkyl groups of 1 to 12 carbon atoms, aryl or halogenated aryl groups of 6 to 12 carbon atoms, or aralkyl groups of 7 to 12 carbon atoms.

Illustrative examples of alkyl groups represented by $R^{12}$ and $R^{13}$ include methyl, ethyl, propyl, butyl, amyl, cyclopentyl, cyclohexyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorobenzene, chlorobenzene, and 1,2,3,4,5-pentafluorobenzene. Exemplary aralkyl groups include benzyl and phenethyl.

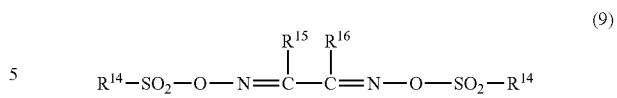  (9)

In the formula, $R^{14}$, $R^{15}$, and $R^{16}$ are straight, branched or cyclic alkyl or halogenated alkyl groups of 1 to 12 carbon atoms, aryl or halogenated aryl groups of 6 to 12 carbon atoms, or aralkyl groups of 7 to 12 carbon atoms. $R^{15}$ and $R^{16}$ may together form a cyclic structure with the proviso that if they form a cyclic structure, each is a straight or branched alkylene group of 1 to 6 carbon atoms.

The alkyl, halogenated alkyl, aryl, halogenated aryl, and aralkyl groups represented by $R^{14}$, $R^{15}$, and $R^{16}$ are exemplified by the same groups mentioned above for $R^{12}$ and $R^{13}$. Examples of alkylene groups represented by $R^{15}$ and $R^{16}$ include methylene, ethylene, propylene, butylene, and hexylene.

Illustrative examples of the photoacid generator include:
onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, and dicyclohexylphenylsulfonium p-toluenesulfonate;

diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n- butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethylglyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

β-ketosulfone derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and imidoyl sulfonate derivatives such as phthalimidoyl triflate, phthalimidoyl tosylate, 5-norbornene-2,3-dicarboxyimidoyl triflate, 5-norbornene-2,3-dicarboxyimidoyl tosylate, and 5-norbornene-2,3-dicarboxyimidoyl n-butylsulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, and tris(p-tert-butoxyphenyl)sulfonium p-toluenesulfonate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; and glyoxime derivatives such as bis-O-(p-toluenesulfonyl)-α-dimethylglyoxime and bis-O-(n-butanesulfonyl)-α-dimethylglyoxime. These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.2 to 15 parts by weight, and especially 0.5 to 8 parts by weight, per 100 parts by weight of all the base resins. At less than 0.2 part, the amount of acid generated during exposure may be too low and the sensitivity and resolution be poor, whereas the addition of more than 15 parts may lower the transmittance of the resist and result in a poor resolution.

Dissolution Inhibitor (D)

To the resist composition, a dissolution inhibitor may be added. The dissolution inhibitor is a compound having on the molecule at least two phenolic hydroxyl groups, in which an average of from 0 to 100 mol % of all the hydrogen atoms on the phenolic hydroxyl groups are replaced with acid labile groups or a compound having on the molecule at least one carboxyl group, in which an average of 10 to 100 mol % of all the hydrogen atoms on the carboxyl groups are replaced with silicon-containing groups of formula (1), both the compounds having an average molecular weight within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid labile groups is on average at least 50 mol %, and preferably at least 70 mol %, of all the carboxyl groups, with the upper limit being 100 mol %.

Preferable examples of such compounds having two or more phenolic hydroxyl groups or compounds having at least one carboxyl group include those of formulas (D1) to (D14) below.

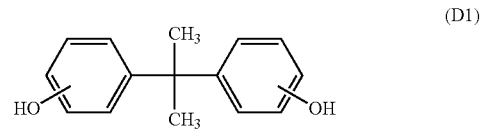

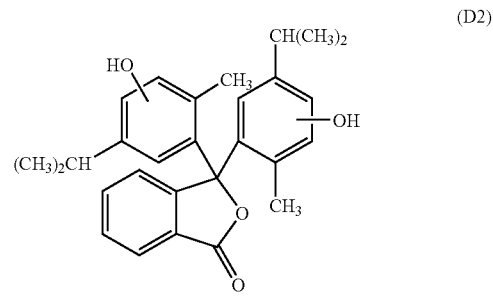

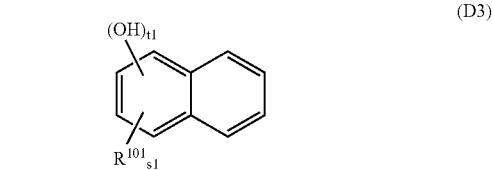

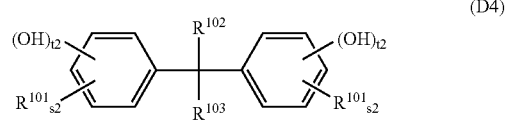

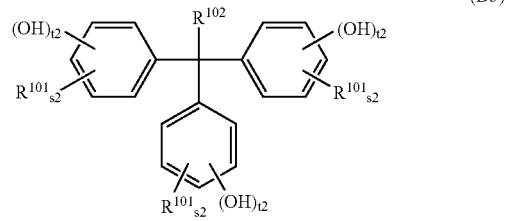

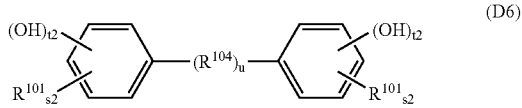

-continued (D7) 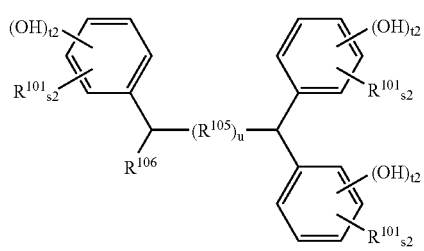

(D8) 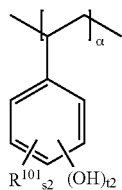

(D9) 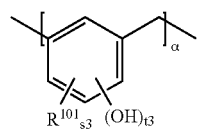

(D10) 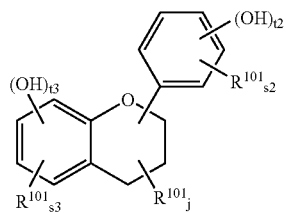

(D11) 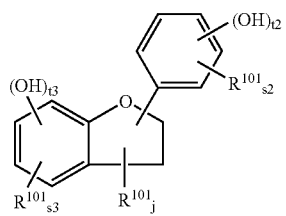

(D12) 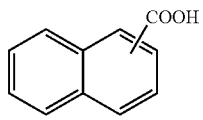

(D13) 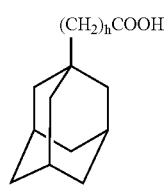

(D14) 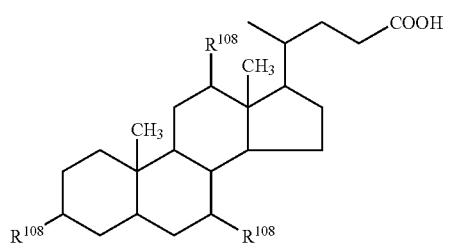

In these formulas, $R^{101}$ and $R^{102}$ are each hydrogen or a straight or branched alkyl or alkenyl of 1 to 8 carbon atoms; $R^{103}$ is hydrogen, a straight or branched alkyl or alkenyl of 1 to 8 carbon atoms, or $-(R^{107})_h-COOH$; $R^{104}$ is $-(CH_2)_i-$ (where i=2 to 10), an arylene of 6 to 10 carbon atoms, carbonyl, sulfonyl, an oxygen atom, or a sulfur atom; $R^{105}$ is an alkylene of 1 to 10 carbon atoms, an arylene of 6 to 10 carbon atoms, carbonyl, sulfonyl, an oxygen atom, or a sulfur atom; $R^{106}$ is hydrogen, a straight or branched alkyl or alkenyl of 1 to 8 carbon atoms, or a hydroxyl-substituted phenyl or naphthyl; $R^{107}$ is a straight or branched alkylene of 1 to 10 carbon atoms; $R^{108}$ is hydrogen or hydroxyl; the letter j is an integer from 0 to 5; u and h are each 0 or 1; s1, t1, s2, t2, s3, and t3 are each numbers which satisfy s1+t1=8, s2+t2=5, and s3+t3=4, and are such that each phenyl skeleton has at least one hydroxyl group; and α is a number such that the compounds of formula (D8) or (D9) have a molecular weight of from 100 to 1,000.

In the above formulas, suitable examples of $R^{101}$ and $R^{102}$ include hydrogen, methyl, ethyl, butyl, propyl, ethynyl, and cyclohexyl; suitable examples of $R^{103}$ include the same groups as for $R^{101}$ and $R^{102}$, as well as $-COOH$ and $-CH_2COOH$; suitable examples of $R^{104}$ include ethylene, phenylene, carbonyl, sulfonyl, oxygen, and sulfur; suitable examples of $R^{105}$ include methylene as well as the same groups as for $R^{104}$; and suitable examples of $R^{106}$ include hydrogen, methyl, ethyl, butyl, propyl, ethynyl, cyclohexyl, and hydroxyl-substituted phenyl or naphthyl.

Basic Compound (E)

The basic compound (E) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile. (See, for example, JP-A 5-232706, JP-A 5-249683, JP-A 5-158239, JP-A 5-249662, JP-A 5-257282, JP-A 5-289322, and JP-A 5-289340).

Examples of suitable basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives. Of these, aliphatic amines are especially preferred.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n- propylamine, tri-iso-propylamine, tri-n-butylamine, tri-isobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, tri-isopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formulas (10) and (11) may also be included.

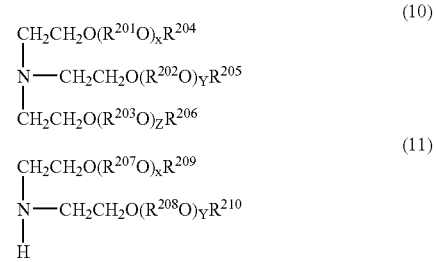

In the formulas, $R^{201}$, $R^{202}$, $R^{203}$, $R^{207}$ and $R^{208}$ independently straight, branched or cyclic alkylenes of 1 to 20 carbon atoms; $R^{204}$, $R^{205}$, $R^{206}$, $R^{209}$ and $R^{210}$ are hydrogen, alkyls of 1 to 20 carbon atoms, or amino; $R^{204}$ and $R^{205}$, $R^{205}$ and $R^{206}$, $R^{204}$ and $R^{206}$, $R^{204}$ with $R^{205}$ and $R^{206}$, and $R^{209}$ and $R^{210}$ may bond together to form rings; and X, Y and Z are each integers from 0 to 20, with the proviso that hydrogen is excluded from $R^{204}$, $R^{205}$, $R^{206}$, $R^{209}$ and $R^{210}$ when X, Y and Z are equal to 0.

The alkylene groups represented by $R^{201}$, $R^{202}$, $R^{203}$, $R^{207}$ and $R^{208}$ preferably have 1 to 20 carbon atoms, more preferably 1 to 10 carbon atoms, and most preferably 1 to 8 carbon atoms. Examples include methylene, ethylene, n-propylene, isopropylene, n-butylene, isobutylene, n-pentylene, isopentylene, hexylene, nonylene, decylene, cyclopentylene, and cyclohexylene.

The alkyl groups represented by $R^{204}$, $R^{205}$, $R^{206}$, $R^{209}$ and $R^{210}$ preferably have 1 to 20 carbon atoms, more preferably 1 to 8 carbon atoms, and most preferably 1 to 6 carbon atoms, and may be straight, branched or cyclic. Examples include methyl, ethyl, n-propyl, isopropyl, n-butyl, isobutyl, tert-butyl, n-pentyl, isopentyl, hexyl, nonyl, decyl, dodecyl, tridecyl, cyclopentyl, and cyclohexyl.

Where $R^{204}$ and $R^{205}$, $R^{205}$ and $R^{206}$, $R^{204}$ and $R^{206}$, $R^{204}$ with $R^{205}$ and $R^{206}$, and $R^{209}$ and $R^{210}$ form rings, the rings preferably have 1 to 20 carbon atoms, more preferably 1 to 8 carbon atoms, and most preferably 1 to 6 carbon atoms, and may have branching alkyl groups of 1 to 6 carbon atoms, and especially 1 to 4 carbon atoms.

X, Y, and Z are each integers from 0 to 20, preferably from 1 to 10, and more preferably from 1 to 8.

Illustrative examples of the compounds of formulas (10) and (11) include tris{2-(methoxymethoxy)ethyl}amine, tris{2-(methoxyethoxy)ethyl}amine, tris[2-{(2-methoxyethoxy)methoxy}ethyl]amine, tris{2-(2-methoxyethoxy)ethyl}amine, tris{2-(1-methoxyethoxy)ethyl}amine, tris{2-(1-ethoxyethoxy)ethyl}amine, tris{2-(1-ethoxypropoxy)

ethyl}amine, tris[2-{(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, and 1-aza-18-crown-6. Especially preferred basic compounds are tertiary amines, aniline derivatives, pyrrolidine derivatives, pyridine derivatives, quinoline derivatives, amino acid derivatives, hydroxyl group-bearing nitrogenous compounds, hydroxyphenyl group-bearing nitrogenous compounds, alcoholic nitrogenous compounds, amide derivatives, imide derivatives, tris{2-(methoxymethoxy)ethyl}amine, tris{2-(2-methoxyethoxy)ethyl}amine, tris[2-{(2-methoxyethoxy)methyl}ethyl]amine, and 1-aza-15-crown-5.

The above-described basic compound may be used singly or in combinations of two or more thereof, and is preferably formulated in an amount of 0.01 to 2 parts by weight, and especially 0.01 to 1 part by weight, per 100 parts by weight of all the base resins. At less than 0.01 part, the desired effects of the basic compound would not be apparent, while the use of more than 2 parts would result in too low a sensitivity.

The resist composition of the invention may include optional ingredients, typically a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, and fluorinated organosiloxane compounds. Useful surfactants are commercially available under the trade names Florade FC-430 and FC-431 from Sumitomo 3M Co., Ltd., Surflon S-141, S-145, S-381 and S-383 from Asahi Glass Co., Ltd., Unidyne DS-401, DS-403 and DS-451 from Daikin Industry Co., Ltd., Megaface F-8151, F-171, F-172, F-173 and F-177 from Dai-Nippon Ink & Chemicals, Inc., and X-70-092 and X-70-093 from Shin-Etsu Chemical Co., Ltd. Preferred surfactants are Florade FC-430 from Sumitomo 3M Co., Ltd. and X-70-093 from Shin-Etsu Chemical Co., Ltd.

Pattern formation using the resist composition of the invention may be carried out by a known lithographic technique. For example, the resist composition is applied onto an organic film on a substrate such as a novolac film of about 0.1 to 10.0 μm thick on a silicon wafer by spin coating or the like to form a resist film having a thickness of 0.1 to 1.0 μm, which is then pre-baked on a hot plate at 60 to 200° C. for 10 seconds to 10 minutes, and preferably at 80 to 150° C. for 30 seconds to 5 minutes. A patterning mask having the desired pattern is then placed over the resist film, and the film is exposed through the mask to an electron beam or high-energy radiation having a wavelength of up to 300 nm such as deep-UV, an excimer laser, or x-rays in a dose of about 1 to 200 mJ/cm$^2$, and preferably about 10 to 100 mJ/cm$^2$, then post-exposure baked (PEB) on a hot plate at 60 to 150° C. for 10 seconds to 5 minutes, and preferably at 80 to 130° C. for 30 seconds to 3 minutes. Development is then carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 10 seconds to 3 minutes, and preferably 30 seconds to 2 minutes. These steps result in the formation of the desired pattern on the substrate. Of the various types of high-energy radiation that may be used, the resist composition of the invention is best suited to micropattern formation with, in particular, deep-UV rays and excimer laser light having a wavelength of 254 to 120 nm, especially KrF excimer laser of 248 nm or ArF excimer laser of 193 nm, x-rays, and an electron beam.

In the developing step, the exposed area of the resist film is dissolved away until the underlying organic film is exposed. Then the exposed area of the organic film is conventionally processed with an oxygen plasma generated by a dry etching apparatus.

The silicon-containing compounds of the invention are polymerizable into polymers suited as a base resin in the bi-layer resist technology. The resist composition comprising a polymer of the silicon-containing compound as a base resin is sensitive to high-energy radiation and has excellent sensitivity and resolution at a wavelength of less than 300 nm, and high resistance to oxygen plasma etching. Because of these advantages, the resist composition is suited for bi-layer resist and easily forms a finely defined pattern having sidewalls perpendicular to the substrate. The resist composition lends itself to micropatterning for the fabrication of VLSIs.

EXAMPLE

Examples are given below for further illustrating the invention although the invention is not limited thereby. The abbreviations used have the following meaning, NMR for nuclear magnetic resonance, GPC for gel permeation chromatography, Mw for weight average molecular weight, and Mn for number average molecular weight.

Polymerizable silicon-containing compounds were synthesized according to the following procedures.

Example 1

Synthesis of Ethyl 2-(trimethylsilylmethyl)acrylate

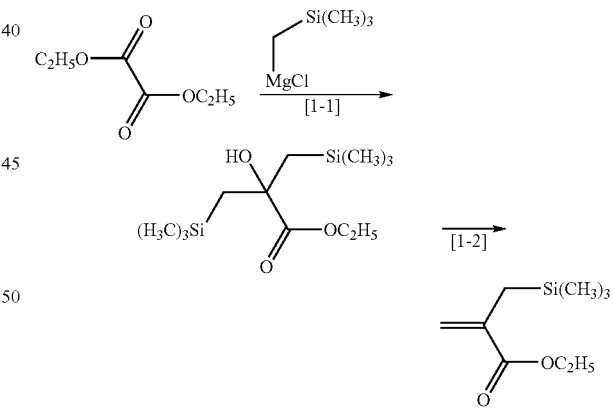

[1-1] Synthesis of ethyl 2-hydroxy-3-trimethylsilyl-2-trimethylsilylmethylpropionate Under a nitrogen atmosphere and with ice cooling, a solution of 293 g diethyl oxalate in 500 ml tetrahydrofuran was slowly added dropwise to a Grignard reagent solution which had been prepared from 540 g of chloromethyltrimethylsilane, 107 g of magnesium and 2,000 ml of tetrahydrofuran. The solution was stirred for 3 hours at room temperature, after which an aqueous solution of ammonium chloride was added for hydrolysis. Usual work-up procedure including extraction, washing, drying and concentration yielded 525 g (crude yield 95%) of ethyl 2-hydroxy-3-trimethylsilyl-2-trimethylsilylmethylpropionate.

GC-MS (EI) (m/z)⁺: 45, 73, 147, 203 [(M minus trimethylsilyl)⁺]

[1-2] Synthesis of Ethyl 2-(trimethylsilylmethyl)acrylate

Route 1:

A mixture of 276 g of ethyl 2-hydroxy-3-trimethylsilyl-2-trimethylsilylmethylpropionate obtained in [1-1] and 120 g of formic acid was stirred at 40° C. for one hour. To the solution was added 1,000 ml of water and the mixture was extracted with n-pentane. Usual work-up procedure including washing, drying and concentration yielded a crude product. It was distilled under reduced pressure, obtaining 182 g (yield 98%) of the desired compound, ethyl 2-(trimethylsilylmethyl)acrylate.

boiling point: 54° C./200 Pa $^1$H-NMR (300 MHz, CDCl$_3$) δ: −0.01 (s, 9H), 1.28 (3H, t, J=7.2 Hz), 1.82 (2H, d, J=1.1 Hz), 4.17 (2H, q, J=7.2 Hz), 5.28 (1H, dt, J=1.7, 1.2 Hz), 5.96 (1H, d, J=1.7 Hz) ppm $^{13}$C-NMR (75 MHz, CDCl$_3$) δ: −1.80, 14.18, 22.15, 60.60, 121.39, 138.63, 167.63 ppm IR (NaCl) vmax: 1718, 1619, 1319, 1299, 1249, 1184, 1101, 852 cm$^{-1}$ Route 2:

In 250 ml of toluene were dissolved 45.8 g of ethyl 2-hydroxy-3-trimethylsilyl-2-trimethylsilylmethylpropionate obtained in [1-1] and 1.0 g of p-toluenesulfonic acid monohydrate. The solution was heated under reflux for one hour. Cooling was followed by usual work-up procedure including washing, drying and concentration. The crude product thus obtained was distilled under reduced pressure, obtaining 18.2 g (yield 59%) of the desired compound, ethyl 2-(trimethylsilylmethyl)acrylate. The spectroscopic and physical properties of this product were identical with those of the product from Route 1.

Route 3:

A mixture of 27.6 g of ethyl 2-hydroxy-3-trimethyl-silyl-2-trimethylsilylmethylpropionate obtained in [1-1] and 250 ml of a solution of 0.5 M sodium ethylate in ethanol was heated under reflux for 5 hours. After cooling, the reaction mixture was poured into water, extracted with n-hexane, followed by usual work-up procedure including washing, drying and concentration. The crude product thus obtained was distilled under reduced pressure, obtaining 8.93 g (yield 48%) of the desired compound, ethyl 2-(trimethylsilylmethyl)-acrylate. The spectroscopic and physical properties of this product were identical with those of the product from Route 1.

Example 2

Synthesis of 2-(trimethylsilylmethyl)acrylic acid

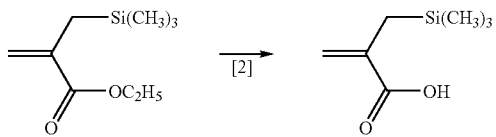

A mixture of 250 g of ethyl 2-(trimethylsilylmethyl)-acrylate obtained in Example 1, 600 g of isopropyl alcohol and 225 g of 25% aqueous sodium hydroxide was stirred at 40° C. for 3 hours. To the reaction mixture was added 1,000 ml of water and the mixture was concentrated on an evaporator. The residue was poured into 260 g of 20% aqueous hydrochloric acid and extracted with n-hexane. Usual work-up procedure including washing, drying and concentration gave 211 g (yield 99%) of the desired compound, 2-(trimethylsilylmethyl)acrylic acid.

$^1$H-NMR (300 MHz, DMSO-d$_6$) δ: −0.03 (s, 9H), 1.77 (2H, d, J=1.0 Hz), 5.32 (1H, dt, J=2.1, 1.0 Hz), 5.86 (1H, d, J=2.1 Hz), 12.30 (1H, br. s) ppm IR (NaCl) vmax: ~2950 (br.), 1695, 1616, 1436, 1249, 1209, 854 cm$^{-1}$ Example 3

Synthesis of t-butyl 2-(trimethylsilylmethyl)acrylate

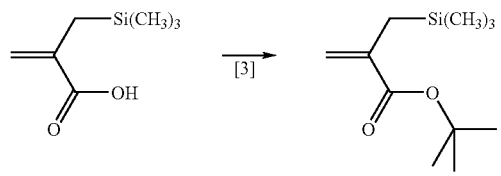

While a mixture of 15.8 g of 2-(trimethylsilylmethyl) acrylic acid obtained in Example 2, 200 ml of diethyl ether, and 0.5 ml of conc. sulfuric acid was stirred at room temperature, isobutylene was bubbled into the mixture for 5 hours at a rate of 10 ml/min. The reaction mixture was washed with an aqueous saturated potassium carbonate solution, concentrated under reduced pressure, and distilled under reduced pressure to give 17.5 g (yield 82%) of the desired compound, t-butyl 2-(trimethylsilylmethyl)acrylate.

boiling point: 57° C./400 Pa $^1$H-NMR (300 MHz, CDCl$_3$) δ: −0.01 (s, 9H), 1.47 (3H, s), 1.78 (2H, d, J=1.0 Hz), 5.21 (1H, dt, J=1.8, 1.1 Hz), 5.88 (1H, d, J=1.9 Hz) ppm $^{13}$C-NMR (75 MHz, CDCl$_3$) δ: −1.78, 22.03, 28.00, 80.20, 120.48, 13.9.98, 166.85 ppm IR (NaCl) vmax: 1712, 1619, 1367, 1328, 1249, 1159, 850 cm$^{-1}$ Example 4

Synthesis of 1-ethylcyclopentyl 2-(trimethylsilylmethyl)-acrylate

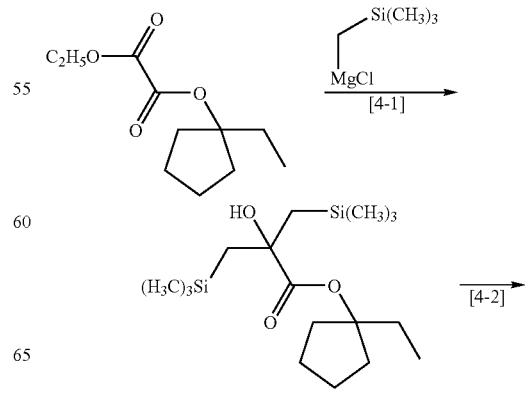

-continued

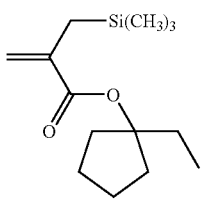

[4-1] Synthesis of 1-ethylcyclopentyl 2-hydroxy-3-trimethylsilyl-2-trimethylsilylmethylpropionate Under a nitrogen atmosphere, a Grignard reagent solution was prepared from 100 g of chloromethyltrimethylsilane, 20 g of magnesium and 500 ml of diethyl ether. Under a nitrogen atmosphere, the Grignard reagent solution was slowly added dropwise to a solution of 80 g of ethyl(1-ethylcyclopentyl) oxalate (which had been prepared by reacting ethyl chloroglyoxylate and 1-ethylcyclopentanol in pyridine) in 360 ml of diethyl ether at −40° C. After 2 hours of stirring at the temperature, the solution was warmed up to room temperature and stirred for further 8 hours. An aqueous solution of ammonium chloride was added for hydrolysis, followed by usual work-up procedure including extraction, washing, drying and concentration to give 102 g (crude yield 79%) of crude 1-ethylcyclopentyl 2-hydroxy-3-trimethylsilyl-2-trimethylsilylmethylpropionate.

GC-MS (EI) (m/z)$^{30}$ : 73, 97, 147, 203, 329

[4-2] Synthesis of 1-ethylcyclopentyl 2-(trimethylsilylmethyl)acrylate

Route 1:

Under a nitrogen atmosphere and at room temperature, a solution of 92 g of 1-ethylcyclopentyl 2-hydroxy-3-trimethylsilyl-2-trimethylsilylmethylpropionate obtained in [4-1] in 100 ml of tetrahydrofuran was added to a suspension of 10.2 g of sodium hydride in 400 ml of tetrahydrofuran. The reaction mixture was stirred for 4 hours while heating under reflux. The reaction mixture was poured into water and extracted with n-hexane. Usual work-up procedure including washing, drying and concentration yielded a crude product. It was purified by silica gel column chromatography and distilled under reduced pressure, obtaining 53.0 g (yield 78%) of the desired compound, 1-ethylcyclopentyl 2-(trimethylsilylmethyl)acrylate.

boiling point: 100° C./330 Pa $^1$H-NMR (300 MHz, CDCl$_3$) δ: −0.01 (s, 9H), 0.86 (3H, t, J=7.4 Hz), 1.50–1.78 (6H, m), 1.79 (2H, d, J=1.0 Hz), 1.99 (2H, q, J=7.4 Hz), 2.06–2.20 (2H, m), 5.24 (1H, dt, J=1.8, 1.1 Hz), 5.89 (1H, d, J=1.9 Hz) ppm $^{13}$C-NMR (75 MHz, CDCl$_3$) δ: −1.76, 8.74, 21.87, 24.08, 29.83, 37.08, 93.41, 120.40, 139.79, 166.91 ppm IR (NaCl) vmax: 1710, 1618, 1330, 1247, 1168, 1101, 852 cm$^{-1}$ Route 2:

With stirring at room temperature, 1.2 g of potassium t-butoxide was added to a mixture of 3.45 g of 1-ethylcyclopentyl 2-hydroxy-3-trimethylsilyl-2-trimethylsilylmethylpropionate obtained in [4-1] and 40 ml of tetrahydrofuran. The reaction mixture was stirred for 16 hours at room temperature, it was then poured into 10% aqueous hydrochloric acid and extracted with ethyl acetate. Usual work-up procedure including washing, drying and concentration gave a crude product, which was purified by silica gel column chromatography to give 1.05 g (yield 41%) of the desired compound, 1-ethylcyclopentyl 2-(trimethylsilylmethyl) acrylate. The spectroscopic and physical properties of this product were identical with those of the product from Route 1.

Route 3:

A mixture of 3.45 g of 1-ethylcyclopentyl 2-hydroxy-3-trimethylsilyl-2-trimethylsilylmethylpropionate obtained in [4-1], 40 ml of acetic acid, and 1.0 g of sodium acetate was stirred for 28 hours at 60° C. The reaction mixture was poured into an aqueous saturated sodium hydrogen carbonate solution and extracted with ethyl acetate, followed by usual work-up procedure including washing, drying and concentration. The crude product thus obtained was purified by silica gel column chromatography, obtaining 0.98 g (yield 38%) of the desired compound, 1-ethylcyclopentyl 2-(trimethylsilylmethyl)acrylate. The spectroscopic and physical properties of this product were identical with those of the product from Route 1.

Example 5

Synthesis of 1-ethylcyclopentyl 2-(trimethylsilylmethyl)-acrylate

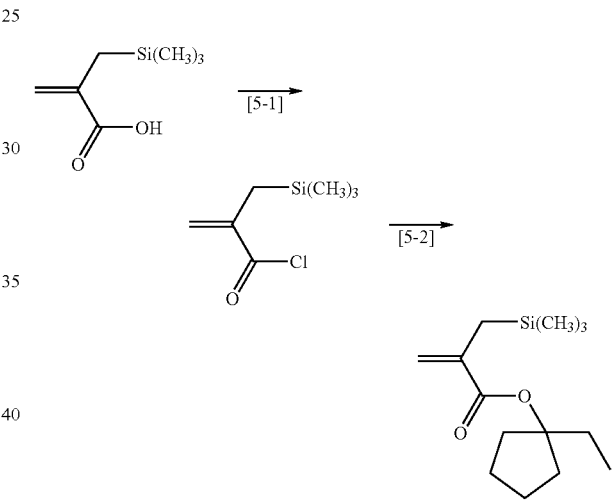

[5-1] Synthesis of 2-(trimethylsilylmethyl)acryloyl chloride

With stirring at 50° C., 60.0 g of oxalyl chloride was slowly added dropwise to a mixture of 69.8 g of 2-(trimethylsilylmethyl)acrylic acid obtained in Example 2 and 300 ml of toluene. Stirring was continued at the temperature. After gas evolution ceased, stirring was continued at 70° C. for 2 hours. After cooling, the product in toluene solution was directly used in the subsequent step.

[5-2]

With stirring at 40° C., the toluene solution of 2-(trimethylsilylmethyl)acryloyl chloride obtained in [5-1] was added dropwise over one hour to a mixture of 60 g of 1-ethylcyclopentanol, 150 g of pyridine, and 1 g of 4-dimethylaminopyridine. The mixture was stirred at 40° C. for 29 hours, poured into 5% aqueous hydrochloric acid, and extracted with n-hexane. Usual work-up procedure including washing, drying and concentration gave a crude product, which was distilled under reduced pressure to yield 102 g (yield 85%) of the desired compound, 1-ethylcyclopentyl 2-(trimethylsilylmethyl)acrylate. The spectroscopic and physical properties of this product were identical with those of the product in Example 4.

Example 6

Synthesis of 2-oxooxolan-3-yl 2-(trimethylsilylmethyl)acrylate

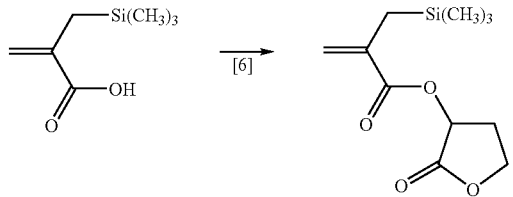

With stirring at room temperature, 26.4 g of α-bromo-γ-butyrolactone was added to a mixture of 15.8 g of 2-(trimethylsilylmethyl)acrylic acid obtained in Example 2, 13.4 g of sodium hydrogen carbonate, 30 g of water, and 60 g of N,N-dimethylformamide. The mixture was stirred at 50° C. for 20 hours, poured into water, and extracted with ethyl acetate. Usual work-up procedure including washing, drying and concentration gave a crude product, which was distilled under reduced pressure to give 18.4 g (yield 65%) of the desired compound, 2-oxooxolan-3-yl 2-(trimethylsilylmethyl)acrylate.

boiling point: 96° C./11 Pa $^1$H-NMR (300 MHz, CDCl$_3$) δ: −0.01 (s, 9H), 1.83 (2H, d, J=1.1 Hz), 2.30 (1H, ddt, J=8.9, 12.9, 9.5 Hz), 2.72 (1H, dddd, J=2.6, 6.5, 8.7, 12.9 Hz), 4.30 (1H, dt, J=6.5, 9.4 Hz), 4.47 (1H, dt, J=2.6, 9.1 Hz), 5.41 (1H, dd, J=8.7, 9.4 Hz), 5.42 (1H, dt, J=1.2, 1.1 Hz), 6.085 (1H, d, J=1.4 Hz) ppm $^{13}$C-NMR (75 MHz, CDCl$_3$) δ: −1.88, 22.03, 28.88, 64.98, 67.94, 123.64, 137.15, 166.32, 172.53 ppm IR (NaCl) vmax: 1793, 1725, 1618, 1317, 1299, 1249, 1168, 1106, 1018, 854 cm$^{-1}$

Example 7

Synthesis of 4,8-dioxatricyclo[4.2.1.0$^{3,7}$]nonan-5-on-2-yl 2-(trimethylsilylmethyl)acrylate

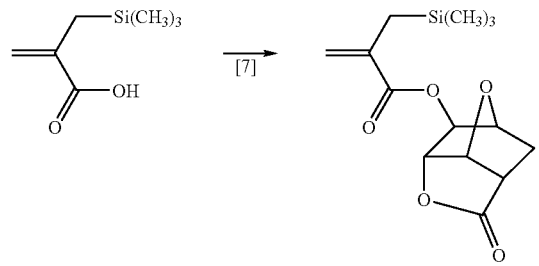

With stirring, a mixture of 15.8 g of 2-(trimethylsilylmethyl)acrylic acid obtained in Example 2, 16.0 g of 2-hydroxy-4,8-dioxatricyclo[4.2.1.0$^{3,7}$]nonan-5-one, 1.0 g of p-toluenesulfonic acid monohydrate, and 800 ml of toluene was heated under reflux for 20 hours while the water formed was being removed. The reaction mixture was cooled and washed with an aqueous saturated sodium hydrogen carbonate solution, followed by usual work-up procedure including drying and concentration. The crude product thus obtained was purified by silica gel chromatography, obtaining 11.8 g (yield 40%) of the desired compound, 4,8-dioxatricyclo[4.2.1.0$^{3,7}$]nonan-5-on-2-yl 2-(trimethylsilylmethyl)acrylate.

GC-MS (EI) (m/z)$^+$: 73, 95, 113, 139, 158, 296 (M$^+$)

GC-MS (CI, methane) (m/z)$^+$: 73, 139, 281, 297 [(M+H)$^+$]

Example 8

Synthesis of 2-[tris(trimethylsilyl)silyl]ethyl 2-(trimethylsilylmethyl)acrylate

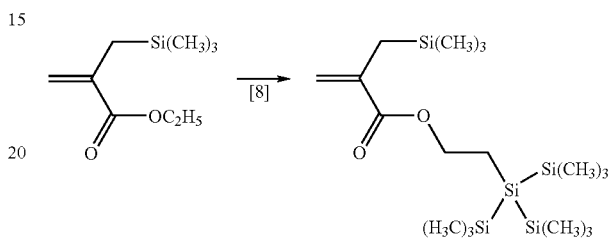

With stirring, a mixture of 15.8 g of ethyl 2-(trimethylsilylmethyl)acrylate obtained in Example 1, 30.0 g of 2-[tris(trimethylsilyl)silyl]ethanol, 300 ml of toluene, and 0.8 g of titanium tetramethoxide was heated under reflux while the ethanol formed was being removed. After ethanol formation was ceased, stirring under heat was continued for further 2 hours. The reaction mixture was directly distilled under reduced pressure, obtaining 39.9 g (yield 92%) of the desired compound, 2-[tris(trimethylsilyl)silyl]ethyl 2-(trimethylsilylmethyl)acrylate.

boiling point: 124° C./9 Pa $^1$H-NMR (300 MHz, CDCl$_3$) δ: −0.00 (s, 9H), 0.19 (27H, s), 1.20–1.29 (2H, m), 1.84 (2H, d, J=1.1 Hz), 4.14–4.23 (2H, m), 5.29 (1H, dt, J=1.1, 1.6 Hz), 5.97 (1H, d, J=1.6 Hz) ppm $^{13}$C-NMR (75 MHz, CDCl$_3$) δ: −1.78, 1.04, 8.80, 22.18, 65.05, 121.24, 138.88, 167.53 ppm IR (NaCl) vmax: 1714, 1619, 1417, 1396, 1315, 1297, 1245, 1172, 1095, 1037, 835 cm$^{-1}$ Silicon-containing polymers were synthesized according to the following procedure.

Example 9

Synthesis of Polymer 1

In 300 ml of tetrahydrofuran were dissolved 21.4 g of t-butyl 2-(trimethylsilylmethyl)acrylate synthesized in Example 3 and 24.2 g of 2-oxooxolan-3-yl 2-(trimethylsilylmethyl)acrylate synthesized in Example 6. Then 1.6 g of 2,2-azibisisobutyronitrile was added thereto. The solution was stirred for 15 hours at 60° C. and then added dropwise to 2,000 ml of n-hexane. The resulting precipitates were collected by filtration, washed with 500 ml of n-hexane, and vacuum dried at 40° C. for 12 hours, obtaining 27.2 g of a polymer shown below as Polymer 1. The yield was 60%. On GPC analysis using polystyrene standards, it had a Mw of 10,000 and a dispersity (Mw/Mn) of 1.65.

Polymer 1
a = 0.50, b = 0.50
Mw = 10,000
Mw/Mn = 1.65

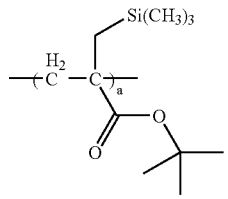

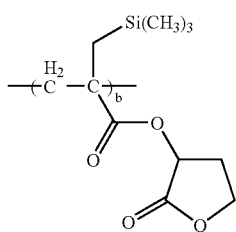

Polymers 2 to 4 were synthesized by similar procedures.

Example 10

Polymer 2
a = 0.50, b = 0.50
Mw = 10,500
Mw/Mn = 1.67

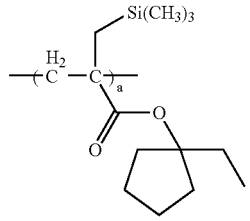

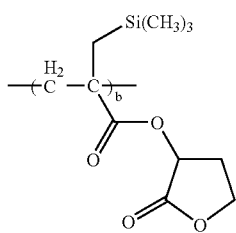

Example 11

Polymer 3
a = 0.40, b = 0.50, c = 0.10
Mw = 11,000
Mw/Mn = 1.66

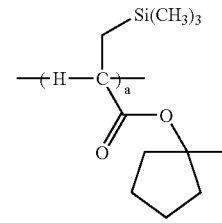

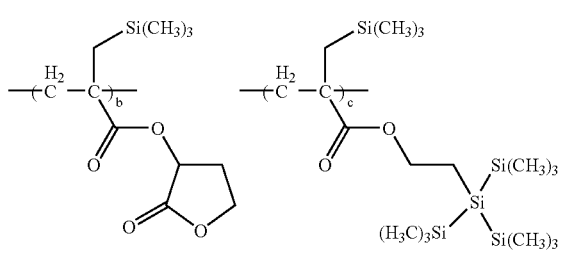

-continued

Example 12

Polymer 4
a = 0.30, b = 0.12, c = 0.58
Mw = 6,000
Mw/Mn = 1.40

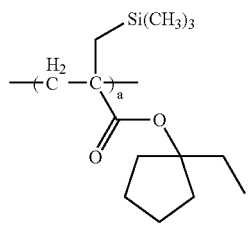

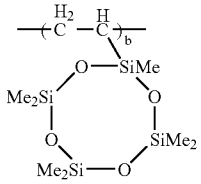 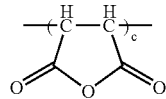

Resist compositions within the scope of the invention were examined for resolution upon KrF excimer laser exposure.

Polymers 1 to 4 as the base resin, triphenylsulfonium trifluoromethanesulfonate as the photoacid generator, and tributylamine as the basic compound were mixed in propylene glycol monomethyl ether acetate (PGMEA) containing 0.01% by weight of surfactant Florade FC-430 (Sumitomo 3M), in accordance with the formulation shown in Table 1. By subsequent filtration through a Teflon filter (pore diameter 0.10 μm), there were prepared resist solutions.

On silicon wafers, lower resist films of 0.5 μm thick were formed by applying novolac resist material OFPR-800 (Tokyo Ohka Kogyo Co., Ltd.) and heating at 300° C. for 5 minutes for curing. Antireflection films of 55 nm thick were formed thereon by spin coating DUV-30 (Brewer Science) and baking at 100° C. for 30 seconds and then at 200° C. for 60 seconds.

On the cured DUV-30/novolac resist/silicon wafer, the resist solutions were spin coated, then baked on a hot plate at 100° C. for 90 seconds to give resist films of 0.2 μm thick. Using a KrF excimer laser stepper (Nikon Corporation, NA 0.60), the resist films were exposed. The resist films were baked (PEB) at 100° C. for 90 seconds and then developed with a 2.38% aqueous solution of tetramethylammonium hydroxide, obtaining positive patterns.

The sensitivity of the resist was the exposure dose (mJ/cm$^2$) which provided a 1:1 line-to-space ratio in a 0.20 μm line-and-space pattern. The resolution of the resist was the minimum line width (μm) of the lines and spaces that separated at this dose.

Using a parallel plate sputter etching apparatus TE-8500 by Tokyo Electron Co., Ltd., the resist films were etched with an etchant, oxygen gas under the following conditions.
Oxygen gas flow rate: 50 sccm
Gas pressure: 1.3 Pa
RF power: 50 W
DC bias: 450 V The lower resist film was etched at a rate of 150 nm/min whereas the inventive resist film was etched at a rate of 15 nm/min or lower. After 2 minutes of etching, those portions of the lower resist film which were not covered with the inventive resist film disappeared completely, leaving a bilayer resist pattern having a thickness of 0.5 μm.

The evaluation results of the resists are shown in Table 1.

TABLE 1

| Example | Base resin (pbw) | Photoacid generator (pbw) | Basic compound (pbw) | Solvent (pbw) | Sensitivity (mJ/cm$^2$) | Resolution (μm) |
|---|---|---|---|---|---|---|
| 13 | Polymer 1 (80) | 3 | 0.1 | 1000 | 26 | 0.18 |
| 14 | Polymer 2 (80) | 3 | 0.1 | 1000 | 20 | 0.16 |
| 15 | Polymer 3 (80) | 3 | 0.1 | 1000 | 28 | 0.17 |
| 16 | Polymer 4 (80) | 3 | 0.1 | 1000 | 20 | 0.17 |

As is evident from Table 1, the resist compositions within the scope of the invention exhibit a high sensitivity and resolution upon KrF excimer laser exposure.

Japanese Patent Application No. 2002-285171 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymerizable silicon-containing compound having the general formula (1):

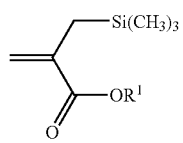

(1)

wherein $R^1$ is a halogen atom or monovalent organic group and $R^1$ is not a tert-butyl group, n-butyl group, methyl group, ethyl group, trimethylsilyl group, triethylsilyl group or benzyl group.

2. A polymerizable silicon-containing ester derivative having an acid eliminatable substituent group and having the general formula (2):

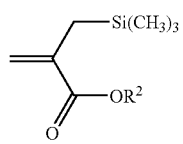

(2)

wherein $R^2$ is an acid labile group and is not a tert-butyl group, trimethylsilyl group or triethylsilyl group.

3. A polymerizable silicon-containing ester derivative having a polar group, having the general formula (3):

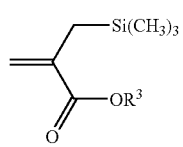

(3)

wherein $R^3$ is a monovalent organic group of 2 to 30 carbon atoms containing an oxygen functional group.

4. A polymerizable silicon-containing ester derivative of formula (3), according to claim 3, wherein the oxygen functional group is selected from the group consisting of hydroxyl, carbonyl, ether bond and ester bond.

5. A polymerizable silicon-containing ester derivative according to claim 4, wherein $R^3$ is selected from the group consisting of straight, branched and cyclic hydrocarbon groups of 2 to 30 carbon atoms having a hydroxyl, alkoxy, carboxyl or alkoxycarbonyl group substituted thereon, and monovalent hydrocarbon groups of 3 to 15 carbon atoms having a lactone structure.

6. A polymerizable silicon-containing ester derivative having a silicon-containing group, having the general formula (4):

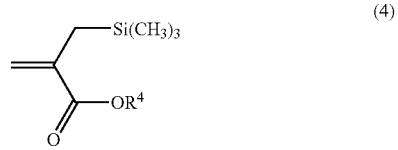

(4)

wherein $R^4$ is a monovalent organic group of 3 to 30 carbon atoms containing at least one silicon atom and $R^4$ is not a trimethylsilyl group or triethylsilyl group.

7. A polymerizable silicon-containing ester derivative according to claim 6, wherein $R^4$ is a silicon-containing organic group of the following formulas:

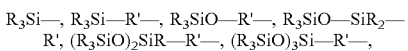

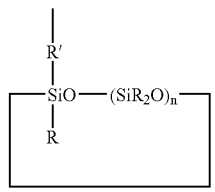

wherein R is an alkyl group of 1 to 20 carbon atoms or an aryl group of 6 to 20 carbon atoms, R' is an alkylene group of 1 to 10 carbon atoms, and the subscript n is at least 2.

8. A polymerizable silicon-containing ester derivative according to claim 7, wherein R is methyl, ethyl or phenyl, R' is an alkylene group of 1 to 5 carbon atoms and the subscript n is 2 to 7.

9. A polymerizable silicon-containing ester derivative according to claim 6, wherein $R^4$ is a silicon-containing organic group of the following formula:

wherein R is an alkyl group of 3 to 20 carbon atoms.

10. A method for preparing a polymerizable silicon-containing compound having the general formula (B), comprising the steps of reacting an oxalate with a trimethylsilylmethyl-metal compound to form a β-hydroxysilyl compound having the general formula (A) and subjecting the β-hydroxysilyl compound to Peterson elimination reaction,

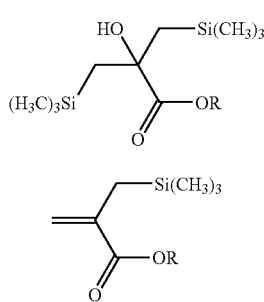

(A)

(B)

wherein R stands for $R^1$, $R^2$, $R^3$ or $R^4$, $R^1$ is a hydrogen atom, halogen atom or monovalent organic group, $R^2$ is an acid labile group, $R^3$ is a monovalent organic group of 2 to 30 carbon atoms containing an oxygen functional group, and $R^4$ is a monovalent organic group of 3 to 30 carbon atoms containing at least one silicon atom.

11. A polymer comprising recurring units of the general formula (1a), (2a), (3a) or (4a) and having a weight average molecular weight of 2,000 to 100,000,

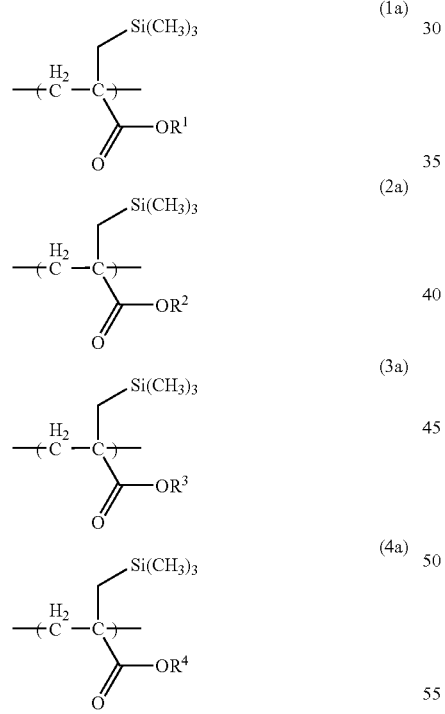

wherein $R^1$ is a hydrogen atom, halogen atom or monovalent organic group, $R^2$ is an acid labile group, $R^3$ is a monovalent organic group of 2 to 30 carbon atoms containing an oxygen functional group, and $R^4$ is a monovalent organic group of 3 to 30 carbon atoms containing at least one silicon atom.

12. The polymer of claim 11 further comprising recurring units of at least one type having the general formula (5a) or (6a):

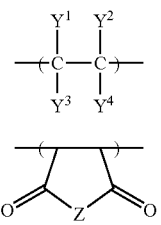

(5a)

(6a)

wherein $Y^1$, $Y^2$, $Y^3$ and $Y^4$ are each independently selected from the group consisting of hydrogen, alkyl groups, aryl groups, halogen atoms, alkoxycarbonyl groups, alkoxycarbonylmethyl groups, cyano groups, fluorinated alkyl groups, and silicon atom-containing monovalent organic groups of 3 to 30 carbon atoms, any two of $Y^1$, $Y^2$, $Y^3$ and $Y^4$ may bond together to form a ring, Z is an oxygen atom or $NR^5$, and $R^5$ is hydrogen, hydroxyl or alkyl.

13. A resist composition comprising the polymer of claim 11.

14. A chemically amplified positive resist composition comprising
   (A) the polymer of claim 11,
   (B) a photoacid generator, and
   (C) an organic solvent.

15. A method for forming a pattern, comprising the steps of:
   applying the positive resist composition of claim 14 onto an organic film on a substrate to form a coating,
   prebaking the coating to form a resist film,
   exposing a circuitry pattern region of the resist film to radiation,
   post-exposure baking the resist film,
   developing the resist film with an aqueous alkaline solution to dissolve away the exposed area, thereby forming a resist pattern, and
   processing the organic film with an oxygen plasma generated by a dry etching apparatus.

16. A polymerizable silicon-containing ester derivative having an acid eliminatable substituent group and having the general formula (2):

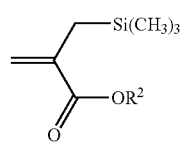

(2)

wherein $R^2$ is an acid labile group selected from the group consisting of the following general formulae (L1) to (L3):

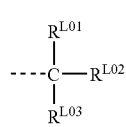

(L1)

-continued

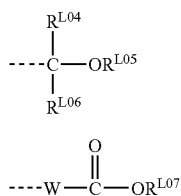
(L2)

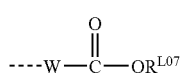
(L3)

wherein the broken line denotes a valence bond, $R^{LO1}$, $R^{LO2}$ and $R^{LO3}$ are each independently a monovalent hydrocarbon group of chain or alicyclic structure having 1 to 20 carbon atoms, which may contain an ether bond, ester bond or sulfide bond and in which some of the hydrogen atoms may be substituted with halogen atoms, hydroxyl groups, alkoxy groups, carbonyl groups, acyloxy groups, cyano groups, a pair of $R^{LO1}$ and $R^{LO2}$, $R^{LO1}$ and $R^{LO3}$, or $R^{LO2}$ and $R^{LO3}$ may bond together to form a ring, when the ring is formed, each of $R^{LO1}$, $R^{LO2}$ and $R^{LO3}$ is a divalent hydrocarbon group of chain or alicyclic structure having 1 to 20 carbon atoms which may contain an ether bond, ester bond or sulfide bond and in which some of the hydrogen atoms may be substituted with halogen atoms, hydroxyl groups, alkoxy groups, carbonyl groups, acyloxy groups, cyano groups, with proviso that $R^{LO1}$, $R^{LO2}$ and $R^{LO3}$ are not methyl groups at the same time, $R^{LO4}$, $R^{LO5}$ and $R^{LO6}$ are each independently hydrogen or a monovalent hydrocarbon group of chain or alicyclic structure having 1 to 20 carbon atoms which may contain an ether bond, ester bond or sulfide bond and in which some of the hydrogen atoms may be substituted with halogen atoms, hydroxyl groups, alkoxy groups, carbonyl groups, acyloxy groups, cyano groups, a pair of $R^{LO4}$ and $R^{LO5}$, $R^{LO4}$ and $R^{LO6}$, or $R^{LO5}$ and $R^{LO6}$ may bond together to form a ring, when the ring is formed, each of $R^{LO4}$, $R^{LO5}$ and $R^{LO6}$ is a divalent hydrocarbon group of chain or alicyclic structure having 1 to 20 carbon atoms which may contain an ether bond, ester bond or sulfide bond and in which some of the hydrogen atoms may be substituted with halogen atoms, hydroxyl groups, alkoxy groups, carbonyl groups, acyloxy groups or cyano groups, $R^{LO7}$ is a group of formula (L1) or (L2), W is a divalent hydrocarbon group of chain or alicyclic structure having 1 to 20 carbon atoms which may contain an ether bond, ester bond or sulfide bond and in which some of the hydrogen atoms may be substituted with halogen atoms, hydroxyl groups, alkoxy groups, carbonyl groups, acyloxy groups or cyano groups.

* * * * *